United States Patent
Mao

(10) Patent No.: US 11,910,803 B2
(45) Date of Patent: Feb. 27, 2024

(54) LACTOBACILLUS PLANTARUM STRAIN IMPARTING HIGH THICKNESS AND/OR HIGH ROPINESS AND/OR HIGH MOUTH THICKNESS TO A DAIRY PRODUCT PRODUCED THEREWITH AND USES THEREOF

(71) Applicant: International N&H Denmark ApS, Kongens Lyngby (DK)

(72) Inventor: Yuejian Mao, Shanghai (CN)

(73) Assignee: INTERNATIONAL N&H DENMARK APS, Lyngby Kongens (DK)

( * ) Notice: Subject to any disclaimer, the term of this patent is extended or adjusted under 35 U.S.C. 154(b) by 536 days.

(21) Appl. No.: 16/651,416

(22) PCT Filed: Sep. 27, 2018

(86) PCT No.: PCT/EP2018/076229
§ 371 (c)(1),
(2) Date: Mar. 27, 2020

(87) PCT Pub. No.: WO2019/063676
PCT Pub. Date: Apr. 4, 2019

(65) Prior Publication Data
US 2020/0288737 A1 Sep. 17, 2020

(30) Foreign Application Priority Data
Sep. 29, 2017 (WO) ................ PCT/CN2017/104287

(51) Int. Cl.
*A23C 9/123* (2006.01)
*A23L 33/145* (2016.01)
(Continued)

(52) U.S. Cl.
CPC .......... *A23C 9/1234* (2013.01); *A23C 9/1322* (2013.01); *A23L 33/145* (2016.08);
(Continued)

(58) Field of Classification Search
CPC ........................... A23C 9/1322; A23L 33/145
See application file for complete search history.

(56) References Cited

U.S. PATENT DOCUMENTS

2012/0156327 A1 * 6/2012 Robichon ............ A23C 19/076
426/43
2014/0322273 A1 10/2014 Ai et al.
(Continued)

FOREIGN PATENT DOCUMENTS

CN       101748083 A       6/2010
CN       102715234 A   *  10/2012
(Continued)

OTHER PUBLICATIONS

Jia et al. "Screening L. plantarum . . . " Food Science and Technology vol. 19 pp. 1045-1050 2013 (Year: 2013).*
(Continued)

*Primary Examiner* — Felicia C Turner

(57) ABSTRACT

The application is directed to a *Lactobacillus plantarum* strain, having the ability to generate a fermented milk presenting a high thickness and/or a high ropiness and/or a high thickness in mouth. The application also concerns a *Lactobacillus plantarum* strain, having the ability to generate a fermented milk presenting a high thickness and/or a high ropiness and/or a high thickness in mouth, further being a low post acidification strain at the temperature of fermentation. The application is also about a method to manufacture fermented product, in particular a fermented dairy product, using a *L. plantarum* strain of the invention or a
(Continued)

bacterial composition, composition or kit-of part comprising a *L. plantarum* strain of the invention.

10 Claims, 4 Drawing Sheets

Specification includes a Sequence Listing.

(51) Int. Cl.
    *A23L 33/175*     (2016.01)
    *A23C 9/13*     (2006.01)
    *C12N 1/20*     (2006.01)
    *C12R 1/25*     (2006.01)

(52) U.S. Cl.
    CPC ............ *A23L 33/175* (2016.08); *C12N 1/205* (2021.05); *A23V 2002/00* (2013.01); *A23V 2400/137* (2023.08); *A23V 2400/169* (2023.08); *C12R 2001/25* (2021.05)

(56) References Cited

U.S. PATENT DOCUMENTS

2017/0042172 A1*   2/2017   Maljaars ............... A23C 9/1238
2017/0258858 A1*   9/2017   Troost ................. G01N 33/5047

FOREIGN PATENT DOCUMENTS

| CN | 104498402 A | 4/2015 |
|---|---|---|
| CN | 105104533 A | 12/2015 |
| WO | WO 2007/095958 A1 | 8/2007 |
| WO | WO-2010034844 A1 * | 4/2010 ......... A61K 47/6901 |
| WO | WO 2011/000879 A2 | 1/2011 |
| WO | WO 2011/000883 A2 | 1/2011 |
| WO | 2011031145 A2 | 3/2011 |
| WO | WO 2011/026863 A1 | 3/2011 |
| WO | WO 2011/161085 A1 | 12/2011 |
| WO | WO 2012/052557 A1 | 4/2012 |
| WO | WO 2013/160270 | 10/2013 |

OTHER PUBLICATIONS

Wang et al., "Characterization of an exopolysaccharide produced by Lactobacillus plantarum YW11 isolated from Tobet Kefir", Carbohydrate Polymers, vol. 125, pp. 16-25 (2015).
Jia et al., "Screening of Lactobacillus plantarum LPM21 with F1F0-ATPase B-subunit mutation used as probiotics adjunct in Sichuan pickle", Food Sci Technol. Res., vol. 19(6), pp. 1045-1050 (2013).
Zhang et al., Acta Microbiologica Sinica, vol. 57(2), pp. 293-303 (Feb. 1, 2017) (abstract only).
International Search Report for PCT/EP2018/076229; international filing date Sep. 27, 2018.
Written Opinion for PCT/EP2018/076229; international filing date Sep. 27, 2018.
International Search Report PCT/CN2017/104287; international filing date Sep. 27, 2017, int. filing date is is Sep. 28, 2017 for '287.
Written Opinion for PCT/CN2017/104287; international filing date Sep. 27, 2017.
Lee et al., "Strain-Specific Features of Extracellular Polysaccharides and Their Impact on Lactobacillus plantarum—Host Interactions", Applied and Environmental Microbiology, vol. 82, No. 13, Jul. 2016, pp. 3959-3970.

* cited by examiner

LACTOBACILLUS PLANTARUM STRAIN IMPARTING HIGH THICKNESS AND/OR HIGH ROPINESS AND/OR HIGH MOUTH THICKNESS TO A DAIRY PRODUCT PRODUCED THEREWITH AND USES THEREOF

CROSS REFERENCE TO RELATED PATENT APPLICATIONS

This specification claims priority under 35 USC § 371 as a national phase of Int'l Patent Appl. PCT/EP2018/076229 (filed Sep. 27, 2018; and published Apr. 4, 2019 as Int'l Publ. No. WO2019/063676), which, in turn, claims priority to PCT/CN2017/104287 (filed Sep. 29, 2017). The entire text of each of the above-referenced patent applications is incorporated by reference into this specification.

FIELD OF THE INVENTION

The application is directed to a *Lactobacillus plantarum* strain, having the ability to generate a fermented milk presenting a high thickness and/or a high ropiness and/or a high thickness in mouth. The application also concerns a *Lactobacillus plantarum* strain, having the ability to generate a fermented milk presenting a high thickness and/or a high ropiness and/or a high thickness in mouth, further being a low post acidification strain at the temperature of fermentation. The application is also about a method to manufacture fermented product, in particular a fermented dairy product, using a *L. plantarum* strain of the invention or a bacterial composition, composition or kit-of part comprising a *L. plantarum* strain of the invention.

BACKGROUND TO THE INVENTION

Traditional starter cultures for fermented milk have been mainly developed for western countries (Europe, North America). The fermentative pathway is typically carried out by two different bacteria: *Streptococcus thermophilus* (ST) and *Lactobacillus delbruekii* subsp. *bulgaricus*.

Texture is a very important quality parameter for fermented milks and consumers continuously request fermented milk products having new taste and/or new texture. Among important texture descriptors for fermented products, high mouthfeel, long texture and smoothness are well liked by many consumers. There is therefore a need to improve the rheological properties of fermented milks.

Improvement of rheological properties of fermented milks can be obtained by the use of thickening agents, such as alginates. However, there is trend for more natural products perceived as healthy by the consumers, with a minimal of added ingredients (additive-free yoghurts).

WO2011/000879 and WO2011/000883 applications describe cultures comprising respectively *Streptococcus thermophilus* and *Lactobacillus fermenturn* strains, and *Streptococcus thermophilus* and *Lactobacillus johnsonii* strains, and their use in the manufacture of low-fat fermented milk products. According to these applications, the replacement of the conventionally used *Lactobacillus delbruekii* subsp. *bulgaricus* by either *Lactobacillus fermentum* or *Lactobacillus johnsonii*—in combination with *Streptococcus thermophilus* strain(s)—would lead to low-fat fermented milk products having improved rheological properties (higher viscosity) and lower post-acidification.

There is still a need for new means to manufacture fermented products with differentiation in texture, in particular high mouth and spoon thickness and high stickiness, while limiting the presence of additives in the fermented products.

SUMMARY OF THE INVENTION

A first aspect of the invention relates to a *Lactobacillus plantarum* strain which—when inoculated into milk—generates a fermented milk presenting a high thickness and/or a high ropiness and/or a high thickness in mouth, in particular presenting one, two or three of the following rheological features, as assayed by test A: a) a shear stress measured at shear rate 11.6 $s^{-1}$ higher than 30 Pa; b) a shear stress measured at shear rate 200 $s^{-1}$ higher than 60 Pa; c) a difference of the shear stress measured at 146 $s^{-1}$ minus the shear stress measured at 41.1 $s^{-1}$ higher than 12.

A second aspect of the invention relates to a *Lactobacillus plantarum* strain which—when inoculated into milk—generates a fermented milk presenting a high thickness and/or a high ropiness and/or high thickness in mouth, and further characterized by being a low post acidification strain at the temperature of fermentation.

A third aspect of the invention relates to a bacterial composition comprising or consisting of a *Lactobacillus plantarum* strain of the invention, in particular in combination with at least another lactic acid bacteria.

A fourth aspect of the invention relates to a composition comprising or consisting of the *L. plantarum* strain of the invention or the bacterial composition of the invention and a booster.

A fifth aspect of the invention relates to a kit-of-part comprising or consisting of the *L. plantarum* strain of the invention or the bacterial composition of the invention and a booster.

A sixth aspect of the invention relates to a method for manufacturing a fermented product, comprising inoculating a substrate with the *L. plantarum* strain of the invention, the bacterial composition of the invention, the composition of the invention or the kit-of part of the invention, and fermenting said inoculated substrate, to obtain a fermented product.

A seventh aspect of the invention relates to a fermented product comprising the *L. plantarum* strain of the invention or obtained or obtainable by a method of the invention. An eight aspect of the invention relates to the use of the *L. plantarum* strain of the invention, the bacterial composition of the invention, the composition of the invention or the kit-of part of the invention, in the manufacture of a fermented dairy product.

DETAILED DESCRIPTION

The inventors have surprisingly identified a lactic acid bacterium which can be used to obtain a fermented milk with unique texture and rheological properties. This lactic acid bacterium is a *Lactobacillus plantarum* strain (*L. plantarum*), and can be used to provide a fermented milk with high thickness and/or high ropiness and/or high thickness in mouth.

The invention is directed to a *Lactobacillus plantarum* strain which—when inoculated into milk—generates a fermented milk presenting one, two or three of the following rheological features, as assayed by test A:
  a) a shear stress measured at shear rate 11.6 $s^{-1}$ higher than 30 Pa;
  b) a shear stress measured at shear rate 200 $s^{-1}$ higher than 60 Pa;
  c) a difference of the shear stress measured at 146 $s^{-1}$ minus the shear stress measured at 41.1 $s^{-1}$ higher than 12.

For the avoidance of doubt, a *Lactobacillus plantarum* strain is defined herein as described in the literature, in particular in Skerman VBD, McGowan V, and Sneath PH; Int. J. Syst. Bacteriol., 30 (1980), 225-420.

The rheological parameters described herein have been assayed using the following Test A (also described in example 2). The shear stress value measured at shear rate 11.6 $s^{-1}$ as defined herein and the shear stress value measured at shear rate 200 $s^{-1}$ as defined herein are—as calculated by Test A—with a standard deviation of ±1 Pa, between replicates within the same experiment. The difference value of the shear stress measured at 146 $s^{-1}$ minus the shear stress measured at 41.1 $s^{-1}$ as defined herein is—as calculated by Test A—with a standard deviation of ±1, between replicates within the same experiment.

Thus, the claimed *Lactobacillus plantarum* strain has the ability to generate a fermented milk presenting a shear stress measured at shear rate 11.6 $s^{-1}$ as defined herein and/or a shear stress measured at shear rate 200 $s^{-1}$ as defined herein and/or a difference of the shear stress measured at 146 $s^{-1}$ minus the shear stress measured at 41.1 $s^{-1}$ as defined herein, measured under the following conditions:

Test A

Figure 8:
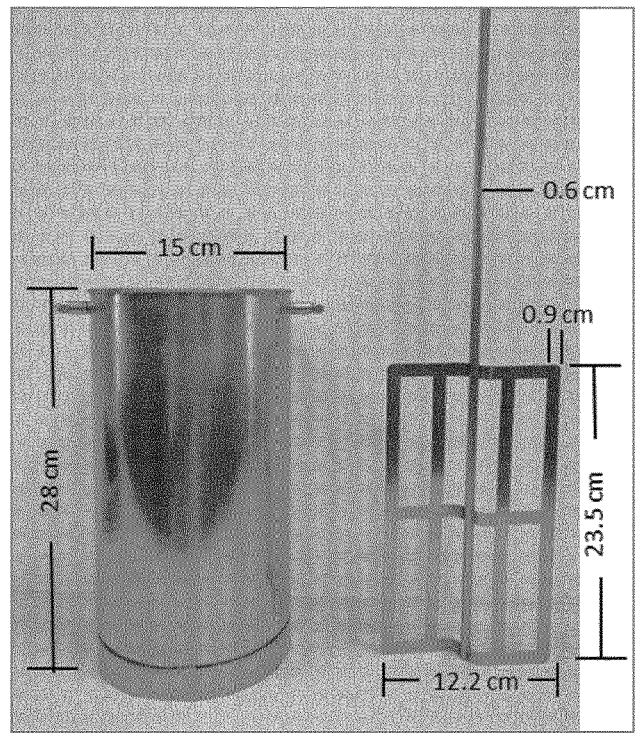
FIG. 8 shows the container used for fermentation and the stirring rake used for the rheology measurements in test A.

2 L UHT milk (3.2% protein, 3.5% fat) added with 6% sucrose and 0.1% of yeast extract powder (LP0021) from Oxoid™ is heat treated at 85° C. for 15 min and cooled down to room temperature. A culture of each strain to be tested is inoculated into milk at 1.10' CFU/mL. The inoculated milk is then fermented at 30° C. to reach pH 4.5 (typically about 22-24 h). After fermentation, the sample is stirred by a rotator (RZR 2051 control, Heidolph) at 100 rpm for 1.5 min and stored at 4° C. overnight, before measurement by rheometer. The used tank and bladder are as disclosed in FIG. 8. The sample is assessed by a rheometer (Anton Paar MCR 302, CC27-SN27450, Austria) using a coaxial cylinder C-CC27-T200/SS and a bob-cup. The rheometer is set to a constant temperature of 10° C. during the measurement. Settings are as follows:
  holding time (to rebuild to somewhat original structure): 10 minutes, without any physical stress applied to the sample.
  25 measuring points over 500 s (one every 20 s)
  rotation step (to measure the shear stress at 11.6 1/s, the shear stress at 200 1/s and the difference of the shear stress at 146 1/s minus the shear stress at 41.1 1/s)
  Two steps are designed:
  Shear rate: d(gamma)/dt=[0.1–200] 1/s log and [200–0.1] 1/s log
  Each step contained 25 measuring points over 500 s (on every 20 s)

The shear stress measured at shear rate 11.6 $s^{-1}$ represents the thickness of the fermented milk. According to the invention, the claimed *Lactobacillus plantarum* strain has the ability to generate a fermented milk presenting a shear stress measured at shear rate 11.6 $s^{-1}$ higher than 30 Pa, as assayed by test A described herein. In a particular embodiment, the claimed *Lactobacillus plantarum* strain has the ability to generate a fermented milk presenting a shear stress measured at shear rate 11.6 $s^{-1}$ higher than 32 Pa. In a particular embodiment, the claimed *Lactobacillus plantarum* strain has the ability to generate a fermented milk presenting a shear stress measured at shear rate 11.6 $s^{-1}$ higher than 35 Pa. In an embodiment, the claimed *Lactobacillus plantarum* strain has the ability to generate a fermented milk presenting a shear stress measured at shear rate 11.6 $s^{-1}$ in the range 30-45 Pa. In a particular embodiment, the claimed *Lactobacillus plantarum* strain has the ability to generate a fermented milk presenting a shear stress measured at shear rate 11.6 $s^{-1}$ in the range 32-40 Pa. The values or ranges of shear stress measured at shear rate 11.6 $s^{-1}$ as described herein are disclosed individually or in combination with any values or ranges of shear stress measured at shear rate 200 $s^{-1}$ described herein and/or any values or ranges of Δ of the shear stress measured at 146 $s^{-1}$—the shear stress measured at 41.1 $s^{-1}$ described herein. These values and ranges are assayed by test A described herein.

The shear stress measured at shear rate 200 $s^{-1}$ represents the coating or the mouth thickness (also called the thickness in mouth) of the fermented milk. According to the invention, the claimed *Lactobacillus plantarum* strain has the ability to generate a fermented milk presenting a shear stress measured at shear rate 200 $s^{-1}$ higher than 60 Pa as assayed by test A described herein. In a particular embodiment, the claimed *Lactobacillus plantarum* strain has the ability to generate a fermented milk presenting a shear stress measured at shear rate 200 $s^{-1}$ higher than 65 Pa. In a particular embodiment, the claimed *Lactobacillus plantarum* strain has the ability to generate a fermented milk presenting a shear stress measured at shear rate 200 $s^{-1}$ higher than 70 Pa. In a particular embodiment, the claimed *Lactobacillus plantarum* strain has the ability to generate a fermented milk presenting a shear stress measured at shear rate 200 $s^{-1}$ higher than 75 Pa. In an embodiment, the claimed *Lactobacillus plantarum* strain has the ability to generate a fermented milk presenting a shear stress measured at shear rate 200 $s^{-1}$ in the range 60-85 Pa. In a particular embodiment, the claimed *Lactobacillus plantarum* strain has the ability to generate a fermented milk presenting a shear stress measured at shear rate 200 $s^{-1}$ in the range 65-85 Pa. In a particular embodiment, the claimed *Lactobacillus plantarum* strain has the ability to generate a fermented milk presenting a shear stress measured at shear rate 200 $s^{-1}$ in the range 70-82 Pa. In a particular embodiment, the claimed *Lactobacillus plantarum* strain has the ability to generate a fermented milk presenting a shear stress measured at shear rate 200 s$^{-1}$ in the range 75-80 Pa. The values or ranges of shear stress measured at shear rate 200 s$^{-1}$ described herein are disclosed individually or in combination with any values or ranges of shear stress measured at shear rate 11.6 s$^{-1}$ as described herein and/or any values or ranges of Δ of the shear stress measured at 146 s$^{-1}$—the shear stress measured at 41.1 s$^{-1}$ described herein. These values and ranges are assayed by test A described herein.

The difference of the shear stress measured at 146 s$^{-1}$ minus the shear stress measured at 41.1 s$^{-1}$ (Δ shear stress 146 s$^{-1}$-41.1 s$^{-1}$) represents the ropiness or stickiness of the fermented milk. According to the invention, the claimed *Lactobacillus plantarum* strain has the ability to generate a fermented milk presenting a Δ shear stress 146 s$^{-1}$-41.1 s$^{-1}$ higher than 12. In a particular embodiment, the claimed *Lactobacillus plantarum* strain has the ability to generate a fermented milk presenting a Δ shear stress 146 s$^{-1}$-41.1 s$^{-1}$ higher than 13. In a particular embodiment, the claimed *Lactobacillus plantarum* strain has the ability to generate a fermented milk presenting a Δ shear stress 146 s$^{-1}$-41.1 s$^{-1}$ higher than 14. In a particular embodiment, the claimed *Lactobacillus plantarum* strain has the ability to generate a fermented milk presenting a Δ shear stress 146 s$^{-1}$-41.1 s$^{-1}$ higher than 15. In an embodiment, the claimed *Lactobacillus plantarum* strain has the ability to generate a fermented milk presenting a Δ shear stress 146 s$^{-1}$-41.1 s$^{-1}$ in the range 12-18. In a particular embodiment, the claimed *Lactobacillus plantarum* strain has the ability to generate a fermented milk presenting a Δ shear stress 146 s$^{-1}$-41.1 s$^{-1}$ in the range 13-17. In a particular embodiment, the claimed *Lactobacillus plantarum* strain has the ability to generate a fermented milk presenting a Δ shear stress 146 s$^{-1}$-41.1 s$^{-1}$ in the range 14-16. The values or ranges of Δ shear stress 146 s$^{-1}$-41.1 s$^{-1}$ described herein are disclosed individually or in combination with any values or ranges of shear stress measured at shear rate 11.6 s$^{-1}$ as described herein and/or any values or ranges of shear stress measured at shear rate 200 s$^{-1}$ described herein. These values and ranges are assayed by test A described herein.

The expression "one, two or three of the [following] rheological features" (in the context of the *L. plantarum* strain, the method, the fermented product or the use) means either:
- one rheological feature selected from the group consisting of a) a shear stress measured at shear rate 11.6 s$^{-1}$ higher than 30 Pa, b) a shear stress measured at shear rate 200 s$^{-1}$ higher than 60 Pa and c) a difference of the shear stress measured at 146 s$^{-1}$ minus the shear stress measured at 41.1 s$^{-1}$ higher than 12, or
- two rheological features selected from the following combinations: 1) a) a shear stress measured at shear rate 11.6 s$^{-1}$ higher than 30 Pa and b) a shear stress measured at shear rate 200 s$^{-1}$ higher than 60 Pa, 2) a) a shear stress measured at shear rate 11.6 s$^{-1}$ higher than 30 Pa and c) a difference of the shear stress measured at 146 s$^{-1}$ minus the shear stress measured at 41.1 s$^{-1}$ higher than 12, or 3) b) a shear stress measured at shear rate 200 s$^{-1}$ higher than 60 Pa and c) a difference of the shear stress measured at 146 s$^{-1}$ minus the shear stress measured at 41.1 s$^{-1}$ higher than 12; or
- three rheological features, i.e., the combination of a) a shear stress measured at shear rate 11.6 s$^{-1}$ higher than 30 Pa, b) a shear stress measured at shear rate 200 s$^{-1}$ higher than 60 Pa and c) a difference of the shear stress measured at 146 s$^{-1}$ minus the shear stress measured at 41.1 s$^{-1}$ higher than 12.

Thus, in an embodiment, the invention concerns a *Lactobacillus plantarum* strain which—when inoculated into milk—generates a fermented milk presenting a) a shear stress measured at shear rate 11.6 s$^{-1}$ higher than 30 Pa, in particular higher than 32 Pa, in particular higher than 35 Pa, or in the range 30-45 Pa, in particular 32-40 Pa.

In an embodiment, the invention concerns a *Lactobacillus plantarum* strain which—when inoculated into milk—generates a fermented milk presenting b) a shear stress measured at shear rate 200 s$^{-1}$ higher than 60 Pa, in particular higher than 65 Pa, in particular higher than 70 Pa, in particular higher than 75 Pa or in the range 60-85 Pa, in particular 65-85 Pa, in particular 70-82 Pa, in particular 75-80 Pa.

In an embodiment, the invention concerns a *Lactobacillus plantarum* strain which—when inoculated into milk—generates a fermented milk presenting c) a difference of the shear stress measured at 146 s$^{-1}$ minus the shear stress measured at 41.1 s$^{-1}$ higher than 12, in particular higher than 13, in particular higher than 14, in particular higher than 15, or in the range 12-19, in particular 13-18, in particular 14-17.

In an embodiment, the invention concerns a *Lactobacillus plantarum* strain which—when inoculated into milk—generates a fermented milk presenting a) a shear stress measured at shear rate 11.6 s$^{-1}$ higher than 30 Pa, in particular higher than 32 Pa, in particular higher than 35 Pa, or in the range 30-45 Pa, in particular 32-40 Pa; and b) a shear stress measured at shear rate 200 s$^{-1}$ higher than 60 Pa, in particular higher than 65 Pa, in particular higher than 70 Pa, in particular higher than 75 Pa or in the range 60-85 Pa, in particular 65-85 Pa, in particular 70-82 Pa, in particular 75-80 Pa. In a particular embodiment, said *Lactobacillus plantarum* strain—when inoculated into milk—generates a fermented milk presenting a) a shear stress measured at shear rate 11.6 s$^{-1}$ higher than 32 Pa and b) a shear stress measured at shear rate 200 s$^{-1}$ higher than 70 Pa. In another particular embodiment, said *Lactobacillus plantarum* strain—when inoculated into milk—generates a fermented milk presenting a) a shear stress measured at shear rate 11.6 s$^{-1}$ in the range 32-40 Pa and b) a shear stress measured at shear rate 200 s$^{-1}$ in the range 70-82 Pa.

In an embodiment, the invention concerns a *Lactobacillus plantarum* strain which—when inoculated into milk—generates a fermented milk presenting a) a shear stress measured at shear rate 11.6 s$^{-1}$ higher than 30 Pa, in particular higher than 32 Pa, in particular higher than 35 Pa, or in the range 30-45 Pa, in particular 32-40 Pa; and c) a difference of the shear stress measured at 146 s$^{-1}$ minus the shear stress measured at 41.1 s$^{-1}$ higher than 12, in particular higher than 13, in particular higher than 14, in particular higher than 15, or in the range 12-19, in particular 13-18, in particular 14-17. In a particular embodiment, said *Lactobacillus plantarum* strain—when inoculated into milk—generates a fermented milk presenting a) a shear stress measured at shear rate 11.6 s$^{-1}$ higher than 32 Pa; and c) a difference of the shear stress measured at 146 s$^{-1}$ minus the shear stress measured at 41.1 s$^{-1}$ higher than 14. In another particular embodiment, said *Lactobacillus plantarum* strain—when inoculated into milk—generates a fermented milk presenting a) a shear stress measured at shear rate 11.6 s$^{-1}$ in the range 32-40 Pa; and c) a difference of the shear stress measured at 146 s$^{-1}$ minus the shear stress measured at 41.1 s$^{-1}$ in the range 14-17.

In an embodiment, the invention concerns a *Lactobacillus plantarum* strain which—when inoculated into milk—generates a fermented milk presenting b) a shear stress measured at shear rate 200 s$^{-1}$ higher than 60 Pa, in particular higher than 65 Pa, in particular higher than 70 Pa, in particular higher than 75 Pa or in the range 60-85 Pa, in particular 65-85 Pa, in particular 70-82 Pa, in particular 75-80 Pa; and c) a difference of the shear stress measured at 146 s$^{-1}$ minus the shear stress measured at 41.1 s$^{-1}$ higher than 12, in particular higher than 13, in particular higher than 14, in particular higher than 15, or in the range 12-19, in particular 13-18, in particular 14-17. In a particular embodiment, said *Lactobacillus plantarum* strain—when inoculated into milk—generates a fermented milk presenting b) a shear stress measured at shear rate 200 s$^{-1}$ higher than 70 Pa; and c) a difference of the shear stress measured at 146 s-1 minus the shear stress measured at 41.1 s-1 higher than 14. In another particular embodiment, said *Lactobacillus plantarum* strain—when inoculated into milk—generates a fermented milk presenting b) a shear stress measured at shear rate 200 s$^{-1}$ in the range 70-82 Pa; and c) a difference of the shear stress measured at 146 s-1 minus the shear stress measured at 41.1 s-1 in the range 14-17.

In an embodiment, the invention concerns a *Lactobacillus plantarum* strain which—when inoculated into milk—generates a fermented milk presenting a) a shear stress measured at shear rate 11.6 s$^{-1}$ higher than 30 Pa, in particular higher than 32 Pa, in particular higher than 35 Pa, or in the range 30-45 Pa, in particular 32-40 Pa; b) a shear stress measured at shear rate 200 s$^{-1}$ higher than 60 Pa, in particular higher than 65 Pa, in particular higher than 70 Pa, in particular higher than 75 Pa or in the range 60-85 Pa, in particular 65-85 Pa, in particular 70-82 Pa, in particular 75-80 Pa; and c) a difference of the shear stress measured at 146 s$^{-1}$ minus the shear stress measured at 41.1 s$^{-1}$ higher than 12, in particular higher than 13, in particular higher than 14, in particular higher than 15, or in the range 12-19, in particular 13-18, in particular 14-17. In a particular embodiment, said *Lactobacillus plantarum* strain—when inoculated into milk—generates a fermented milk presenting a) a shear stress measured at shear rate 11.6 s$^{-1}$ higher than 32 Pa; b) a shear stress measured at shear rate 200 s$^{-1}$ higher than 70 Pa; and c) a difference of the shear stress measured at 146 s-1 minus the shear stress measured at 41.1 s-1 higher than 14. In another particular embodiment, said *Lactobacillus plantarum* strain—when inoculated into milk—generates a fermented milk presenting a) a shear stress measured at shear rate 11.6 s$^{-1}$ in the range 32-40 Pa; b) a shear stress measured at shear rate 200 s$^{-1}$ in the range 70-82 Pa; and c) a difference of the shear stress measured at 146 s-1 minus the shear stress measured at 41.1 s-1 in the range 14-17.

Any *Lactobacillus plantarum* strain fulfilling one, two or three of the rheological feature(s) defined herein is part of the invention. The invention has been exemplified with the DSM32493 strain, deposited at the DSMZ. There is no reason to doubt that other *L. plantarum* strains sharing one, two or three of the rheological feature (s) defined herein with the DSM32493 strain exist, with the possibility of using the DSM32493 strain as a positive control.

In a particular embodiment, the invention is directed to the *Lactobacillus plantarum* strain DSM32493 deposited at the DSMZ on Apr. 26, 2017.

In a particular embodiment, the invention also concerns a variant of DSM32493. By "variant of DSM32493 strain", it means a *Lactobacillus plantarum* strain derived from the DSM32493 strain and which generates a fermented milk presenting one, two or three of the rheological features described herein (as assayed by test A), i.e., one, two or three of the following rheological features: a) a shear stress measured at shear rate 11.6 s$^{-1}$ as defined herein and/or b) a shear stress measured at shear rate 200 s$^{-1}$ as defined herein and/or c) a difference of the shear stress measured at 146 s$^{-1}$ minus the shear stress measured at 41.1 s$^{-1}$. In a particular embodiment, the DSM32493 strain variant as defined herein is able to generate a fermented milk presenting, as assayed by test A, a) a shear stress measured at shear rate 11.6 s$^{-1}$ (thickness) higher than 30 Pa; b) a shear stress measured at shear rate 200 s$^{-1}$ (coating/mouth thickness) higher than 60 Pa; and c) a difference of the shear stress measured at 146 s$^{-1}$ minus the shear stress measured at 41.1 s$^{-1}$ (ropiness/stickiness) higher than 12. In a particular embodiment, the DSM32493 strain variant as defined herein is able to generate a fermented milk presenting, as assayed by test A, a) a shear stress measured at shear rate 11.6 s$^{-1}$ (thickness) higher than 32 Pa; b) a shear stress measured at shear rate 200 s$^{-1}$ (coating/mouth thickness) higher than 70 Pa; and c) a difference of the shear stress measured at 146 s$^{-1}$ minus the shear stress measured at 41.1 s$^{-1}$ (ropiness/stickiness) higher than 14. In a particular embodiment, the DSM32493 strain variant keeps the properties of the DSM32493 strain, with respect to generating a fermented milk presenting the three rheological features, as assayed by test A, a) a shear stress measured at shear rate 11.6 s$^{-1}$ as defined herein, b) a shear stress measured at shear rate 200 s$^{-1}$ as defined herein and c) a difference of the shear stress measured at 146 s$^{-1}$ minus the shear stress measured at 41.1 s$^{-1}$ as defined herein. By "keep the properties", it is meant that the values of the rheological features obtained using the DSM32493 variant are at least the values obtained using the DSM32493 strain. The definitions and specific embodiments detailed for the rheological features under the *L. plantarum* strain characterization apply similarly in the context of any variant of DSM32493 strain, in particular for but not limited to, the minimal values and ranges of the shear stress measured at shear rate 11.6 s$^{-1}$, the minimal values and ranges of the shear stress measured at shear rate 200 s$^{-1}$, the minimal values and ranges of the shear stress measured at 146 s$^{-1}$ minus the shear stress measured at 41.1 s$^{-1}$, and any individual rheological feature or combination of these rheological features.

A variant of DSM32493 is herein defined as a *Lactobacillus plantarum* strain presenting at least one mutation, such as the addition, deletion, insertion and/or substitution of at least one nucleotide in its genome as compared to the DSM32493 strain. In a particular embodiment, the genome sequence of the variant has an identity of at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% to the genome sequence of the DSM32493 strain. Such a variant can be for example:

- a natural variant obtained spontaneously from the DSM32493 strain after incubation in a selection medium. A natural variant is thus obtained without any genetic manipulation but only by spontaneous mutation of the strain and selection of the strain in an appropriate medium; an example of protocol used to select particular mutants of the DSM32493 strain is disclosed in example 5; or
- a variant comprising at least one mutation in its genome, said mutation being induced by genetic engineering, for instance by directed mutagenesis or random mutagenesis. Random mutagenesis can be performed with UV radiations or mutagenic compounds such as nitrous acid, ethyl-methanesulfonate, NMethyl-N'-nitro-N-nitrosoguanidine, N-ethyl-N-nitrosourea, acridine orange, proflavine.

The invention is also directed to a *Lactobacillus plantarum* as defined herein (including variant of the DSM32493 strain), which—in addition to provide a fermented milk presenting one, two or three of the following rheological features, as assayed by test A, a) a shear stress measured at shear rate 11.6 s$^{-1}$ higher than 30 Pa as defined herein; b) a shear stress measured at shear rate 200 s$^{-1}$ higher than 60 Pa as defined herein; c) a difference of the shear stress measured at 146 s$^{-1}$ minus the shear stress measured at 41.1 s$^{-1}$ higher than 12 as defined herein—is further characterized by being a low post-acidification strain at fermentation temperature.

By "low post acidification strain at fermentation temperature", it is meant a *L. plantarum* strain of the invention which—when inoculated into milk—generates a fermented milk, the pH of which—after fermentation—does not fluctuate more than 0.3 unit when the fermented milk is kept at the fermentation temperature, in particular as assayed by test B (see below). The acidification kinetics is determined by the continuous recording of the pH as a function of time, for example using a Cinac system (CINAC, an automated system for control of lactic starters; Corrieu G, Picque D, Perret B, Quemener P; Process Magazine; 1992: 1068; p.24-27). The acidification kinetics of milk inoculated with the low post-acidification *L. plantarum* strain of the invention and brought at the fermentation temperature follows a two-phase profile, comprising an initial period of sigmoidal pH decrease down to a pH value between 4.0 and 5.0 (to generate the fermented milk), followed by a second period in which the pH value does not fluctuate more than 0.3 unit (when the fermented milk is kept at the fermentation temperature). To characterize the low post acidifying feature of the *L. plantarum* strain of the invention, the pH is measured once the fermentation step terminates (end of the initial period), the fermented milk is kept at the fermentation temperature, the pH is measured at least 48 hours later, and the evolution of the pH (difference) is measured. In a particular embodiment, the fermentation temperature is 37° C.

In an embodiment, the pH obtained at the end of the initial period is comprised between 4.0 and 5.0. In a particular embodiment, the pH obtained at the end of the initial period is comprised between 4.2 and 4.8. In a particular embodiment, the pH obtained at the end of the initial period is comprised between 4.3 and 4.7. In a particular embodiment, the pH obtained at the end of the initial period is comprised between 4.4 and 4.6.

In a particular embodiment, the low post-acidification strain of the invention is able to generate a fermented milk, the pH of which does not fluctuate more than 0.3 unit, in particular not more than 0.2 unit, in particular not more than 0.1 unit, when kept at the fermentation temperature for a period of 48 hours after the end of the initial period.

In a particular embodiment, the low post acidifying feature characterization is carried out, by assaying Test B described below (see also example 5):

Test B

UHT milk (3.2% protein, 3.5% fat) added with 6% sucrose and 0.1% of yeast extract powder (LP0021) from Oxoid™ is heat treated at 85° C. for 15 min and cooled down to room temperature. A culture of each strain to be tested is inoculated into milk at $1.10^7$ CFU/mL and the inoculated milk placed at 37° C. (t=0). The inoculated milk is fermented until a pH of 4.5 is reached ($t_{pH\,4.5}$) and kept at 37° C. for at least 48 hours, and the pH of the milk continuously monitored. The delta pH ($\Delta$pH=pH at ($t_{pH4.5}$+48h)—pH 4.5) is used to represent the post-acidification at fermentation temperature.

In a particular embodiment of a low post-acidification strain of the invention is a *L. plantarum* strain having at least one mutation in its ATP-synthase operon (for example point mutation, deletion, insertion, . . . ), such that the strain has a reduced H$^+$-ATPase activity. The wild-type sequence of the ATP-synthase operon is as set forth in SEQ ID NO:1. The person skilled in the art knows how to determine whether this operon is mutated and how to measure the H$^+$-ATPase activity of a bacterium [see for example Jaichumjai et al. 2010; Food Microbiology 27 (2010) 741-748]. In a particular embodiment, a low post-acidification *L. plantarum* strain of the invention as defined herein has at least one mutation in the ATP synthase alpha subunit gene of the ATP-synthase operon (herein referred as "the ATP synthase alpha subunit gene"). In a particular embodiment, a low post-acidification *L. plantarum* strain of the invention as defined herein has at least one mutation in the ATP synthase alpha subunit gene of the ATP-synthase operon as defined in SEQ ID NO:2. In a particular embodiment, in combination with the previous embodiment on SEQ ID NO:2 or not, the ATP synthase alpha subunit gene of the low post-acidification *L. plantarum* strain of the invention as defined herein encodes a ATP synthase alpha subunit protein having an aspartic acid residue at position 169. In a particular embodiment, the ATP synthase alpha subunit protein of the low post-acidification *L. plantarum* strain of the invention as defined herein is as defined in SEQ ID NO:5. In a particular embodiment, in combination with the previous embodiment on SEQ ID NO:2 or not, the ATP synthase alpha subunit gene of the low post-acidification *L. plantarum* strain of the invention as defined herein bears the mutation G to A at its position 506 (changing the glycine residue at position 169 by an aspartic acid residue). In a particular embodiment, the ATP synthase alpha subunit gene of the low post-acidification *L. plantarum* strain of the invention as defined herein is as defined in SEQ ID NO:4 (wherein the codon GGT at positions 505-507 is changed to GAT).

In an embodiment, the invention is directed to a low post-acidification variant as defined herein, which is a variant of the *Lactobacillus plantarum* strain DSM32493 deposited at the DSMZ on Apr. 26, 2017. In a particular embodiment, the invention is directed to a low post-acidification variant of the *Lactobacillus plantarum* strain DSM32493, wherein said variant bears a mutation in the ATP synthase alpha subunit gene (as compared to the DSM32493 strain), in particular bears the mutation G to A at position 506.

The definitions and specific embodiments detailed for the rheological features under the *L. plantarum* strain characterization (including the variant of DSM32493 strain) apply similarly in the context of the low post-acidification variant, in particular for but not limited to, the minimal values and ranges of the shear stress measured at shear rate 11.6 s-1, the minimal values and ranges of the shear stress measured at shear rate 200 s-1, the minimal values and ranges of the shear stress measured at 146 s-1 minus the shear stress measured at 41.1 s-1, and any individual rheological feature or combination of these rheological features.

The invention is also directed to a bacterial composition comprising or consisting of a *L. plantarum* strain of the invention (in particular a low post-acidification *L. plantarum* strain of the invention). In a particular embodiment, the bacterial composition is a pure culture, i.e., comprises or consists of a single bacterium strain. In another embodiment, the bacterial composition is a mixed culture, i.e., comprises or consists of the *L. plantarum* strain of the invention and at least one other bacterium strain. Thus, in an embodiment, a bacterial composition of the invention comprises or consists of a *L. plantarum* strain of the invention and at least one lactic acid bacterium, in particular at least another *Lactobacillus plantarum* strain and/or a *Lactobacillus delbrueckii* subsp *bulgaricus* strain. By "at least" (in reference to bacterium strain, lactic acid bacterium or another *Lactobacillus plantarum* strain), it is meant 1 or more, and in particular 1, 2, 3, 4 or 5 strains. Thus, in an embodiment, the composition of the invention comprises or consists of—in addition to the *L. plantarum* strain of the invention, 1, 2, 3, 4 or 5 strains, in particular 1, 2, 3, 4 or 5 lactic acid bacteria strains. In a particular embodiment, the bacterial composition of the invention does not contain *Streptococcus thermophilus* strain(s).

In a particular embodiment, the bacterial composition as defined herein, either as a pure or mixed culture as defined above is under frozen, dried, freeze-dried, liquid or solid format, in the form of pellets or frozen pellets, or in a powder or dried powder. In a particular embodiment, the bacterial composition of the invention is in a frozen format or in the form of pellets or frozen pellets, in particular contained into one or more box or sachet. In another embodiment, the bacterial composition as defined herein is under a powder form, such as a dried or freeze-dried powder, in particular contained into one or more box or sachet.

In a particular embodiment, the bacterial composition of the invention, either as a pure culture or mixed culture as defined above, and whatever the format (frozen, dried, freeze-dried, liquid or solid format, in the form of pellets or frozen pellets, or in a powder or dried powder) comprises the *L. plantarum* strain of the invention in a concentration comprised in the range of $10^5$ to $10^{12}$ cfu (colony forming units) per gram of the bacterial composition. In a particular embodiment, the concentration of the *L. plantarum* within the bacterial composition of the invention is in the range of $10^7$ to $10^{12}$ cfu per gram of the bacterial composition, and in particular at least $10^7$, at least $10^8$, at least $10^9$, at least $10^{10}$ or at least $10^{11}$ CFU/g of the bacterial composition. In a particular embodiment, when in the form of frozen or dried concentrate, the concentration of the *Lactobacillus plantarum* strain—as pure culture or as a mixed culture—within the bacterial composition is in the range of $10^8$ to $10^{12}$ cfu/g of frozen concentrate or dried concentrate, and more preferably at least $10^8$, at least $10^9$, at least $10^{10}$, at least $10^{11}$ or at least $10^{12}$ cfu/g of frozen concentrate or dried concentrate.

The invention is also directed to a composition or a kit-of-part comprising or consisting of a *L. plantarum* strain of the invention (in particular a low post-acidification *L. plantarum* strain of the invention) or a bacterial composition as defined herein (such as pure or mixed culture) and a booster. In a particular embodiment, said booster is a yeast extract or an amino-acid containing composition. In a particular embodiment, the booster is a yeast extract, such as a yeast extract powder. Any yeast extract (or powder) can be used, for example but not limited to the yeast extract powder LP0021 from Oxoid™.

The expression "A composition comprising or consisting of a *L. plantarum* strain of the invention or a bacterial composition of the invention and a booster" means that the *L. plantarum* or the bacterial composition and the booster are physically mixed together. The booster amount within the composition is such that the booster is inoculated into milk in the range of 0.001% to 2%. In an embodiment, the composition is under frozen format or in the form of frozen pellets. In another embodiment, the composition is under dried or freeze-dried format or in the form of a powder or dried powder. In contrast, the expression "A kit-of-part comprising or consisting of a *L. plantarum* strain of the invention or a bacterial composition of the invention and a booster" means that the *L. plantarum* or the bacterial composition and the booster are physically separated but intended to be used together. Thus, the *L. plantarum* or the bacterial composition and the booster are in different boxes or sachets. In an embodiment, the *L. plantarum* or the bacterial composition and the booster are both under frozen format or in the form of frozen pellets. In another embodiment, the *L. plantarum* or the bacterial composition and the booster are both under dried or freeze-dried format or in the form of a powder or dried powder.

The invention also concerns a method for manufacturing a fermented product, comprising a) inoculating a substrate with a *L. plantarum* strain of the invention (in particular a low post-acidification *L. plantarum* strain of the invention) and b) fermenting said inoculated substrate, to obtain a fermented product. In a particular embodiment, the *L. plantarum* strain of the invention is inoculated as a bacterial composition as defined herein, such as a pure culture or a mixed culture. In an embodiment, the *L. plantarum* strain of the invention is inoculated as a composition as defined herein, i.e., step a) comprises or consists in inoculating the bacterial composition as defined herein. In another embodiment, the *L. plantarum* strain of the invention is inoculated as a kit-of-part as defined herein i.e., step a) comprises or consists in a1) inoculating the *L. plantarum* strain (or the bacterial composition) and a2) inoculating the booster, wherein the *L. plantarum* strain (or the bacterial composition) and the booster are inoculated simultaneously, or wherein the *L. plantarum* strain (or the bacterial composition) is inoculated before the booster or wherein the booster is inoculated before the *L. plantarum* strain (or the bacterial composition). In a particular embodiment, the method of the invention does not comprise inoculation of *Streptococcus thermophilus* strain(s). In a particular and preferred embodiment, the substrate is inoculated in step a) with a pure culture of the *L. plantarum* strain of the invention.

When booster is used, the booster is inoculated into milk in the range of 0.001% to 2%. In a particular embodiment, the booster is inoculated into milk in the range of 0.01 to 1%. In a particular embodiment, the booster is inoculated into milk in the range of 0.05 to 0.5%.

The fermentation time and temperature are parameters which are dependent upon the wanted final fermented product. In an embodiment, the fermentation temperature is comprised between 30 and 45° C., in particular 32 and 42° C., in particular between 35 and 39° C. The time of fermentation is determined according to the final pH desired at the end of the fermentation, and is comprised between 6 and 75 hours, in particular between 12 and 20 hours. Thus, in an embodiment, the fermentation is carried out until a pH comprised between 4.0 and 5.0, in particular between 4.2 and 4.8, in particular between 4.3 and 4.7, in particular between 4.4 and 4.6, is obtained.

Any substrate can be used in the method of the invention. Thus, in a particular embodiment, the substrate is selected in the group consisting of milk, milk of vegetal origin (such as soy milk) or cereal flour.

In a particular embodiment, the substrate used in the method of the invention is milk substrate. Thus, in an embodiment, the invention is directed to a method for manufacturing a fermented milk product comprising a) inoculating a milk substrate with a *L. plantarum* strain of the invention (in particular a low post-acidification *L. plantarum* strain of the invention) or a bacterial composition as defined herein or a composition as defined herein or a kit-of-part as defined herein; and b) fermenting said inoculated milk substrate, to obtain a fermented milk product. By "milk substrate", it is meant milk of animal origin. In a particular embodiment, the milk substrate originates from cow, goat, sheep, buffalo, zebra, horse, donkey, or camel, and the like. The milk may be in the native state, a reconstituted milk or a skimmed milk.

In another embodiment, the substrate is of plant origin, and can be obtained from extracts of plant material. In a particular embodiment, the substrate is soy, such as soy milk. In another embodiment, the substrate is cereal flour.

The invention is also directed to a fermented product, which is obtained using a *L. plantarum* strain of the invention (in particular a low post-acidification *L. plantarum* strain of the invention) or a bacterial composition of the invention or a composition of the invention or a kit-of-part of the invention, in particular obtained or obtainable by the method of the invention. Thus, the invention is directed to a fermented product comprising the *L. plantarum* strain of the invention (in particular a low post-acidification *L. plantarum* strain of the invention). In a particular embodiment, the *L. plantarum* of the invention is the only bacterium found in the fermented product of the invention. In a particular embodiment, the *L. plantarum* of the invention is the only acidifying bacterium found in the fermented product of the invention.

In a particular embodiment, the fermented product of the invention is a fermented dairy product, in particular a fermented dairy food product or a fermented dairy feed product. In a particular embodiment, the fermented dairy food product of the invention is fresh fermented milk.

In a particular embodiment, the fermented product of the invention is a fermented soy product. In a particular embodiment, the fermented product of the invention is a fermented cereal product.

In a particular embodiment, the fermented product of the invention—in particular the fermented dairy food product as defined herein—contains the DSM32493 strain deposited at the DSMZ on Apr. 26, 2017 or any variant thereof as defined herein. In a particular embodiment, the fermented product of the invention—in particular the fermented dairy food product as defined herein—contains any *L. plantarum* variant of the DSM32493 strain able to generate a fermented milk presenting, as assayed by test A, a) a shear stress measured at shear rate 11.6 s$^{-1}$ higher than 30 Pa as defined herein; b) a shear stress measured at shear rate 200 s$^{-1}$ higher than 60 Pa as defined herein; and c) a difference of the shear stress measured at 146 s$^{-1}$ minus the shear stress measured at 41.1 s$^{-1}$ higher than 12 as defined herein. In a particular embodiment, the fermented product of the invention—in particular the fermented dairy food product as defined herein—contains any *L. plantarum* variant of the DSM32493 strain keeping 1, 2 or 3, of the rheological features of the DSM32493 strain. In a particular embodiment, the fermented product of the invention—in particular the fermented dairy food product as defined herein—contains any *L. plantarum* variant of the DSM32493 strain keeping the rheological features of the DSM32493 strain. In a particular embodiment, the fermented product of the invention—in particular the fermented dairy food product as defined herein—contains a low post-acidification variant as defined herein of the *Lactobacillus plantarum* strain DSM32493. In a particular embodiment, the fermented product of the invention—in particular the fermented dairy food product as defined herein—contains a low post-acidification variant of the *Lactobacillus plantarum* strain DSM32493 deposited at the DSMZ on Apr. 26, 2017, wherein said variant bears a mutation in the ATP synthase alpha subunit gene (as compared to the DSM32493 strain), in particular bears the mutation G to A at its position 506, in particular wherein its ATP synthase alpha subunit gene is as defined in SEQ ID NO:4.

The definitions and specific embodiments detailed for the rheological features under the *L. plantarum* strain characterization apply similarly in the context of the fermented dairy product of the invention, in particular for but not limited to, the minimal values and ranges of the shear stress measured at shear rate 11.6 s$^{-1}$, the minimal values and ranges of the shear stress measured at shear rate 200 s$^{-1}$, the minimal values and ranges of the shear stress measured at 146 s$^{-1}$ minus the shear stress measured at 41.1 s$^{-1}$, and any individual rheological feature or combination of these rheological features. Similarly, the definitions and specific embodiments detailed for the *L. plantarum* strain characterization apply similarly in the context of the fermented dairy product of the invention, in particular for but not limited to, the DSM32493 variant, the low post-acidification variant and the mutation of the ATP synthase alpha subunit gene, in particular the mutation G to A at its position 506, in particular the ATP synthase alpha subunit gene as defined in SEQ ID NO:4.

The invention is also directed to the use of the *L. plantarum* strain of the invention (in particular a low post-acidification *L. plantarum* strain of the invention) or the bacterial composition of the invention or the composition or the kit-of part of the invention, in the manufacture of a fermented dairy product.

In a particular embodiment, the *L. plantarum* strain is the DSM32493 strain deposited at the DSMZ on Apr. 26, 2017 or any variant thereof as defined herein, in particular a low post-acidification variant of the *Lactobacillus plantarum* strain DSM32493 as defined herein, in particular a low post-acidification variant of the *Lactobacillus plantarum* strain DSM32493 bearing a mutation in the ATP synthase alpha subunit gene. The definitions and specific embodiments detailed for the *L. plantarum* strain characterization apply similarly in the context of the use of the invention, in particular for but not limited to, the DSM32493 variant, the low post-acidification *L. plantarum* and the mutation of the ATP synthase alpha subunit gene, in particular the mutation G to A at its position 506, in particular the ATP synthase alpha subunit gene as defined in SEQ ID NO:4.

```
SEQUENCES
SEQ ID NO: 1: L. plantarum ATP-synthase operon
GTGGGTGATCCAGTTCCTACAGTCAAATTCCTTGGACTGACGTTTAATAT

CGCGAATGACATCTCAGTAATTGTGACTTGTCTGATTGTTTTCTTGTTTG

TTTTTTTACTTTCGCGACATTTAACAATGAAGCCCAAGGGTGGACAAAAT

GTGCTGGAGTGGCTCATCGAGTTCACGAATGGCATTGTCAAAGGGTCGAT

CAAGGGTAACGAAGCGTCTAACTTCGGTTTGTACGCATTTACATTGTTTC

TCTTTATCTTCATCGCTAACCAACTTGGATTGTTCATTCACGTTCAGGTC

GGGCAGTATACGTATCTGAAGAGTCCAACCGCCGATCCGATTGTGACTTT

GACGTTATCGTTTATGACCGTTGCACTTGCACATGCTGCGGGTGTTCGTA
```

-continued

AGAAAGGTATGGGTGGTTATTTGAAAGAATACACACAACCTTTTGCTGTT
TTCTCGGTTGTTAACGTCTTTGAACAATTTACCGATTTCCTAACTTTAGG
TCTTCGGCTGTTCGGGAACATCTTTGCTGGTGAAATGTTACTAACGAAGG
TTGCTGATTTGGCAAAGAGCAACGGTTGGTTGAGCTATGTTTACTCATTT
CCAATTGAACTCTTATGGCAAGGTTTCTCAGTGTTTATCGGGAGCATTCA
AGCGTTCGTGTTCGTAACCTTGACTTCAGTTTATATTTCTCAGAAGGTTA
ACGACGAGGAATAATTTCTAGTTTTTTAATTTTAAGGAGGATACACAGAT
TATGGGAGCAATTGCTGCAGGTATTGCTATGTGTGGTGCCGCTATAGGTG
CTGGTATTGGTAACGGTTTGGTTATTTCTAAGATGCTTGAAGGGATGGCC
CGTCAACCAGAATTATCTGGTCAATTACGGACTAACATGTTCATCGGTGT
TGGGTTGGTCGAATCAATGCCTATAATTTCCTTCGTTGTTGCTTTGATGG
TTATGAACAAGTAATCATTGGTCAACGAGTTCATTTAATGAAAATGAAA
GAAGGAGGTGTCATTAGATGCTCTCGCATTTAATTATCGGTGCATCCGGT
CTCTACCTTGGTGATATGTTGTTTATCGGGATTAGCTTTATTGTTTTGAT
GGCATTGATCTCTGTTGTTGCTTGGAAGCCCATCACAAAAATGATGGCTG
ATCGAGCCGACAAGATTGCGAACGACATTGATTCAGCACAAAAGTCTCGG
CAAGAAGCGAGTGACTTAGCTGATCAACGGCGTGATGCGCTATCACACTC
TCGCGCTGAAGCGAGTGAAATTGTCGCTGACGCGAAAAAGAGTGGCGAAA
AGCAACGGTCAAGTATCATTGCCGATGCGCAAAACGAAGCAACGCAGTAT
AAACAAAATGCGCGTAAGGATATTGAACAGGAGCGTCAAGATGCCTTGAA
GAACGTCCAATCAGACGTCGCTGACATTTCGATTGCGATTGCTACGAAGA
TTATTAAGAAGCAATTGGATCCGGAAGGCCAACAGGCATTAATTAATTCG
TATATTGAAGGGTTGGGAAAGCATGAGTCTTGATAATCTTACAATTGCAA
GTCGTTATTCAAAGGCACTCTTTGAACTTGCAGTTGAAAAAGATCAGACC
GAAGCATTCCTGGCCGAGTTAAAGCAATTACGGCAAGTCTTTGTCGACAA
CCCGCAATTGGCAGAGGTCCTCTCAGGATCATTGCTTCCGGTTGATCAAA
AACAGACAACGTTGTCAACTTTGACTGACCACGCTTCAGAATACATTAAA
AACTTTATTCAAATGTTGTATGATTACGGCCGCATGTCGAACTTAGTTGG
CATTGTTGACGCGTTTGAAGCACGTTTCGATGAGAGTCGCAAAATAGTGC
ATGCCGAAGTAACGTCTGCGGTCAAGTTGTCAGATGAGCAAGCTGATGCA
ATCGCAAAGGCATTCGCCAAACGTGTTGGGGCCAATCAGGTTGTTTTGTC
ACGTAAAGTCGATGAAGCAATCATTGGCGGTGTAATTGTGAAGTCAAATA
ATCAAACGTTTGATGGTAGCGTTGCGTTACAACTAACGAATTTAAGACGA
GCACTCATCAACAATTAGTTTACGAAGAGGTGAAACTTTTATGAGCATTA
AATCTGAAGAAATCAGTGCTCTAATCAAACAACAATTAGAAAGTTATCAA
ACTGAGCTCTCAGTTGCTGAAACCGGTACTGTCACCTACGTTGGTGATGG
GATCGCCCGTGCTCACGGACTCGACAACGCCTTACAAGGTGAATTACTCG
AATTCAGTAACGGAGTTTACGGGATGGTACAAAACCTCGAAAGCAACGAT
GTTGGTATCGTTGTTTTAGGGGATTTTGATGGTATTCGTGAAGGCGATAC
TGTTAAGCGGACTGGCCGCATCATGGAAGTTCCAGTCGGTGACGCCATGA
TTGGCCGGGTCGTTAACCCATTAGGTCAACCAGTTGACGGTTCAGGTGAG

-continued

ATTAAGACCACGAATACGCGGCCAATCGAACATAAAGCTCCTGGTATTAT
GCAACGGCAATCAGTTAGCGAACCACTTCAAACTGGGATCAAGGCCATTG
ATGCCTTAGTTCCAATTGGTCGGGGCCAACGTGAATTGATTATCGGTGAC
CGTAAGACTGGGAAGACGTCCGTTGCCATTGATGCCATTTTGAACCAAAA
GGACCAAGACATGATTTGTGTCTACGTTGCAATCGGTCAAAAGGACTCAA
CTGTACGGGCCCAAGTTGAAACGTTGAAGAAGTTAGGTGCGATGGACTAC
ACAATCGTTGTAACTGCCGGACCTGCTGAACCAGCGCCATTACTGTACTT
AGCTCCTTATGCTGGGGCAGCGATGGGTGAAGAATTTATGATGAACGGCA
AGCACGTTTTGATCGTCTATGATGACCTTTCAAAGCAAGCAACGGCTTAC
CGTGAACTTTCCTTGATCCTCCGTCGTCCTCCAGGTCGTGAAGCTTATCC
TGGGGATGTCTTCTACTTGCACTCACGGTTACTCGAACGGGCTGCCAAGT
TGAGCGATGAATTGGGTGGCGGTTCAATGACGGCCTTACCAATTATCGAA
ACGCAAGCTGGGGATATTTCGGCTTATATTCCAACTAACGTTATTTCAAT
CACCGATGGGCAAATCTTCTTGGATAGTGATTCATTCTATTCAGGTGTGC
GGCCAGCGATTGATGCCGGGGCCTCTGTTTCCCGGGTTGGTGGGGATGCG
CAAATTAAAGCGATGAAGTCCGTTGCCGGGACCTTGCGTCTTGACTTGGC
TTCTTATCGTGAATTGGAATCCTTCTCACAATTCGGTTCTGACTTGGATG
CTGCAACCCAAGCGAAATTAAATCGTGGGCAACGGATCGTTGAAGTCTTA
AAACAACCTGTTCATTCACCATTGAAGGTCGAAGAACAAGTAATGATTTT
ATATGCTTTGACCAACGGTTATTTGGATAAAGTGGCAGTTGATGATATTG
CCCGTTACCAAAGTGAATTGTTTGAATTTATTCATGCTAGTCATCAGGAC
CTCTTTGATACGATTTTGGCAACCAAGAAGTTACCAGAAGCTGATAAGAT
GAATGGGGCCTTAGATGCGTTTGCAGAACAATTCCAGCCAACCGCTGCCG
CTGCGAAGTAGTTATGGCTGAAAAGGATGGTGAGTAGTGCATGGCAGAAT
CATTAATGGATGTCAAGCGCCGAATTGACTCAACAAAGAAGACTCATCAA
ATTACGTCGGCAATGCAAATGGTCTCAACTTCAAAATTGAACCAGATTCA
AAAGCATACCAGCACGTATCAGGTGTACGCTTCTAAAGTTGAAAGCATCG
TTTCACATCTTGCCAAAGCTCATCTGATGTCAGCAAGTGCCGGTGTTGCT
AACAGTAATTCGAACACGATTTCAGTTAGTGAATTGCTCGCGCAACGCCC
CGTTAAAAAGACTGGTTTATTGGTGATCACTTCGGACCGTGGCCTCGTTG
GTAGTTACAACAGTAACGTGTTGAAACAGACTAACGATTTCATGCGGACG
CACAAGGTTGATGCCGATAACGCAGTCGTTTTGGCGGTTGGTGGCACTGG
TGCGGATTTCTATAAAAAGAACGGGTTAAACGTGGCTTATGAGTACCGCG
GCGTCTCTGATGTCCCAACTTTTAAAGAGGTTCGTGAAATCGTTAAGACA
GTCACATCAATGTACCACAACGAAGTCTTTGATGAACTTACGTCTTCTA
CAACCACTTTATTAATCGGCTCTCTTCTGGTTTTCGGGCCGTTAAGATGT
TACCGATCTCCGAAGAGACCTTTGAACAAAGTGAGTCAGATAATCGTAAA
GCCAAGGATAGCCGGGTAGATGTCGGTCCCGAGTATGAAATGGAACCGTC
AGAAGAAGCCATTTTGTCGGCCGTGTTGCCACAATATGCTGAAAGCTTGG
TTTATGGTGCAATCTTGGATGCCAAGACTGCTGAACATGCTTCGTCGTCA

ACCGCGATGAAGGCTGCATCAGATAACGCTGGCGATTTAATCGATAAATT
AAATCTGAAATATAACCGTGCGCGTCAAGCTGCTATTACCACTGAAATCA
CTGAAATCACTGGTGGTTTGGTTGCGCAAGAATAACGAAGTGGGAGGAAT
TAACGACTAATGAGTACAGGTAAAGTTGTACAAGTTATTGGACCCGTTGT
TGACGTTGAATTCTCTCTAAACGATAAGTTACCCGATATTAATAACGCCT
TGATCATTCAGAAGGACAACGATGACACTTTAACGGTGGAAGTATCGTTG
GAATTAGGTGATGGGGTTGTTCGGACCGTCGCGATGGATGGTACGGATGG
CTTGCGCCGGGGAATGACAGTTGAAGACACTGGTTCTTCAATTACTGTTC
CCGTTGGTAAAGAGACGTTAGGCCGGGTCTTCAACGTTTTAGGGGAAACC
ATTGATGGTGGTCCAGAATTCGGTCCAGACGCAGAACGTAACCCGATTCA
TCGGGATGCGCCTAAATATGATGAATTAACGACCAGTACTGAAGTATTGG
AAACTGGAATTAAAGTTATTGACCTCTTAGCACCTTATGTTCGTGGTGGT
AAGATTGGGTTGTTCGGTGGTGCCGGTGTTGGTAAAACTGTTTTAATCCA
GGAATTAATTCATAACATTGCCCAAGAACATAACGGGATTTCCGTGTTTA
CCGGTGTTGGTGAACGGACGCGTGAAGGGAATGACCTTTACTTCGAAATG
AAGGCTTCCGGCGTTTTGAAGAATACCGCCATGGTTTATGGTCAAATGAA
CGAACCACCTGGTGCCCGGATGCGGGTGGCCTTGACCGGTTTGACGATTG
CGGAATACTTCCGTGATGTTCAAGGTCAAGACGTGTTGTTATTCATCGAC
AATATCTTCCGGTTCACGCAAGCTGGTTCTGAAGTTTCCGCCTTACTTGG
TCGGATTCCTTCAGCCGTTGGTTACCAACCAACCTTAGCCACTGAAATGG
GTCAATTACAAGAACGGATCACTTCTACCAAGAAGGGGTCAGTTACTTCG
ATTCAAGCCGTTTATGTACCTGCCGATGATTATACCGACCCGGCACCTGC
AACGACTTTCGCCCATTTGGATGCGACGACCAACTTGGAACGTTCTTTGA
CGGAACAAGGGATCTACCCAGCCGTTGACCCATTAGCTTCTTCTTCAATC
GCTCTGGACCCATCAATCGTGGGCGAAGAACATTATCAAGTTGCAACGGA
AGTTCAACGGGTCTTGCAACGTTATCGTGAATTGCAAGATATTATCTCGA
TTTTAGGGATGGATGAATTATCTGACGAAGAAAAGACAACTGTTGCGCGT
GCACGGCGGATTCAATTCTTCTTGTCACAAAACTTCTTCGTTGCCGAAAA
CTTTACGGGCCAACCTGGTTCGTATGTGCCAATCAACGATACCATCAAGG
GCTTCAAAGAAATTCTTGAAGGTAAATATGATGACCTACCAGAAGACGCA
TTCCGTCAAGTTGGTAAGATCGACGACGTGGTCGAAAAAGCGAAATCGAT
GGTAACTGATTAGGAGGGGTTTACATGGCTGACAATGCAAAATCATTAAC
CGTTAGCATCGTAACTCCAGACGGTCAGGTCTATGAGAATAAGACGCCAA
TGTTGATCGTGCGAACGATTGACGGCGAACTCGGAATTTTGCCGAACCAT
ATTCCTGTGATTGCATCGCTTGCAATCGATGAGGTTCGGATCAAGCAACT
TGAAAGTGATCAGGAAGATGACGAAATTGCCGTTAATGGTGGTTTTGTT
AGTTCAGTAATAATACGGCAACGATTGTTGCCGATAGTGCTGAACGTCAG
AATGACATTGACGTTGCTCGAGCTGAAAATGCACGGAAACGCGCTGAAAC
ACGGATTCAAAATGCCCAACAAAAGCACGATGATGCTGAGTTGGCGCGGG
CCCAAGTCGCTTTGCGGCGTGCCATGAACCGTTTGAATGTTGCTCGGCAT
TAA

SEQ ID NO: 2: ATP synthase alpha
subunit gene of the DSM32493 strain
ATGAGCATTAAATCTGAAGAAATCAGTGCTCTAATCAAACAACAATTAGA
AAGTTATCAAACTGAGCTCTCAGTTGCTGAAACCGGTACTGTCACCTACG
TTGGTGATGGGATCGCCCGTGCTCACGGACTCGACAACGCCTTACAAGGT
GAATTACTCGAATTCAGTAACGGAGTTTACGGGATGGTACAAAACCTCGA
AAGCAACGATGTTGGTATCGTTGTTTTAGGGGATTTTGATGGTATTCGTG
AAGGCGATACTGTTAAGCGGACTGGCCGCATCATGGAAGTTCCAGTCGGT
GACGCCATGATTGGCCGGGTCGTTAACCCATTAGGTCAACCAGTTGACGG
TTCAGGTGAGATTAAGACCACGAATACGCGGCCAATCGAACATAAAGCTC
CTGGTATTATGCAACGGCAATCAGTTAGCGAACCACTTCAAACTGGGATC
AAGGCCATTGATGCCTTAGTTCCAATTGGTCGGGGCAACGTGAATTGAT
TATCGGTGACCGTAAGACTGGGAAGACGTCCGTTGCCATTGATGCCATTT
TGAACCAAAAGGACCAAGACATGATTTGTGTCTACGTTGCAATCGGTCAA
AAGGACTCAACTGTACGGGCCAAGTTGAAACGTTGAAGAAGTTAGGTGC
GATGGACTACACAATCGTTGTAACTGCCGGACCTGCTGAACCAGCGCCAT
TACTGTACTTAGCTCCTTATGCTGGGGCAGCGATGGGTGAAGAATTTATG
ATGAACGGCAAGCACGTTTTGATCGTCTATGATGACCTTTCAAAGCAAGC
AACGGCTTACCGTGAACTTTCCTTGATCCTCCGTCGTCCTCCAGGTCGTG
AAGCTTATCCTGGGGATGTCTTCTACTTGCACTCACGGTTACTCGAACGG
GCTGCCAAGTTGAGCGATGAATTGGGTGGCGGTTCAATGACGGCCTTACC
AATTATCGAAACGCAAGCTGGGGATATTTCGGCTTATATTCCAACTAACG
TTATTTCAATCACCGATGGGCAAATCTTCTTGGATAGTGATTCATTCTAT
TCAGGTGTGCGGCCAGCGATTGATGCCGGGGCCTCTGTTTCCCGGGTTGG
TGGGGATGCGCAAATTAAAGCGATGAAGTCCGTTGCCGGGACCTTGCGTC
TTGACTTGGCTTCTTATCGTGAATTGGAATCCTTCTCACAATTCGGTTCT
GACTTGGATGCTGCAACCCAAGCGAAATTAAATCGTGGGCAACGGATCGT
TGAAGTCTTAAAACAACCTGTTCATTCACCATTGAAGGTCGAAGAACAAG
TAATGATTTTATATGCTTTGACCAACGGTTATTTGGATAAAGTGGCAGTT
GATGATATTGCCCGTTACCAAAGTGAATTGTTTGAATTTATTCATGCTAG
TCATCAGGACCTCTTTGATACGATTTTGGCAACCAAGAAGTTACCAGAAG
CTGATAAGATGAATGGGGCCTTAGATGCGTTTGCAGAACAATTCCAGCCA
ACCGCTGCCGCTGCGAAGTAG SEQ ID NO: 3: ATP synthase alpha
subunit protein of the DSM32493 strain
MSIKSEEISALIKQQLESYQTELSVAETGTVTYVGDGIARAHGLDNALQG
ELLEFSNGVYGMVQNLESNDVGIVVLGDFDGIREGDTVKRTGRIMEVPVG
DAMIGRVVNPLGQPVDGSEIKTTNTRPIEHKAPGIMQRQSVSEPLQTGI
KAIDALVPIGRGQRELIIGDRKTGKTSVAIDAILNQKDQDMICVYVAIGQ
KDSTVRAQVETLKKLGAMDYTIVVTAGPAEPAPLLYLAPYAGAAMGEEFM
MNGKHVLIVYDDLSKQATAYRELSLILRRPPGREAYPGDVFYLHSRLLER
AAKLSDELGGGSMTALPIIETQAGDISAYIPTNVISITDGQIFLDSDSFY

```
SGVRPAIDAGASVSRVGGDAQIKAMKSVAGTLRLDLASYRELESFSQFGS

DLDAATQAKLNRGQRIVEVLKQPVHSPLKVEEQVMILYALTNGYLDKVAV

DDIARYQSELFEFIHASHQDLFDTILATKKLPEADKMNGALDAFAEQFQP

TAAAAK

SEQ ID NO: 4: ATP synthase alpha subunit gene of a
low post-acidification mutant of DSM32493 strain
ATGAGCATTAAATCTGAAGAAATCAGTGCTCTAATCAAACAACAATTAGA

AAGTTATCAAACTGAGCTCTCAGTTGCTGAAACCGGTACTGTCACCTACG

TTGGTGATGGGATCGCCCGTGCTCACGGACTCGACAACGCCTTACAAGGT

GAATTACTCGAATTCAGTAACGGAGTTTACGGGATGGTACAAAACCTCGA

AAGCAACGATGTTGGTATCGTTGTTTTAGGGGATTTTGATGGTATTCGTG

AAGGCGATACTGTTAAGCGGACTGGCCGCATCATGGAAGTTCCAGTCGGT

GACGCCATGATTGGCCGGGTCGTTAACCCATTAGGTCAACCAGTTGACGG

TTCAGGTGAGATTAAGACCACGAATACGCGGCCAATCGAACATAAAGCTC

CTGGTATTATGCAACGGCAATCAGTTAGCGAACCACTTCAAACTGGGATC

AAGGCCATTGATGCCTTAGTTCCAATTGGTCGGGGCCAACGTGAATTGAT

TATCGATGACCGTAAGACTGGGAAGACGTCCGTTGCCATTGATGCCATTT

TGAACCAAAAGGACCAAGACATGATTTGTGTCTACGTTGCAATCGGTCAA

AAGGACTCAACTGTACGGGCCCAAGTTGAAACGTTGAAGAAGTTAGGTGC

GATGGACTACACAATCGTTGTAACTGCCGGACCTGCTGAACCAGCGCCAT

TACTGTACTTAGCTCCTTATGCTGGGGCAGCGATGGGTGAAGAATTTATG

ATGAACGGCAAGCACGTTTTGATCGTCTATGATGACCTTTCAAAGCAAGC

AACGGCTTACCGTGAACTTTCCTTGATCCTCCGTCGTCCTCCAGGTCGTG

AAGCTTATCCTGGGGATGTCTTCTACTTGCACTCACGGTTACTCGAACGG

GCTGCCAAGTTGAGCGATGAATTGGGTGGCGGTTCAATGACGGCCTTACC

AATTATCGAAACGCAAGCTGGGGATATTTCGGCTTATATTCCAACTAACG

TTATTTCAATCACCGATGGGCAAATCTTCTTGGATAGTGATTCATTCTAT

TCAGGTGTGCGGCCAGCGATTGATGCCGGGGCCTCTGTTTCCCGGGTTGG

TGGGGATGCGCAAATTAAAGCGATGAAGTCCGTTGCCGGGACCTTGCGTC

TTGACTTGGCTTCTTATCGTGAATTGGAATCCTTCTCACAATTCGGTTCT

GACTTGGATGCTGCAACCCAAGCGAAATTAAATCGTGGGCAACGGATCGT

TGAAGTCTTAAAACAACCTGTTCATTCACCATTGAAGGTCGAAGAACAAG

TAATGATTTTATATGCTTTGACCAACGGTTATTTGGATAAAGTGGCAGTT

GATGATATTGCCCGTTACCAAAGTGAATTGTTTGAATTTATTCATGCTAG

TCATCAGGACCTCTTTGATACGATTTTGGCAACCAAGAAGTTACCAGAAG

CTGATAAGATGAATGGGGCCTTAGATGCGTTTGCAGAACAATTCCAGCCA

ACCGCTGCCGCTGCGAAGTAG

SEQ ID NO: 5: ATP synthase alpha subunit
protein of a low post-acidification mutant
of DSM32493 strain
MSIKSEEISALIKQQLESYQTELSVAETGTVTYVGDGIARAHGLDNALQG

ELLEFSNGVYGMVQNLESNDVGIVVLGDFDGIREGDTVKRTGRIMEVPVG

DAMIGRVVNPLGQPVDGSGEIKTTNTRPIEHKAPGIMQRQSVSEPLQTGI

KAIDALVPIGRGQRELIIDDRKTGKTSVAIDAILNQKDQDMICVYVAIGQ

KDSTVRAQVETLKKLGAMDYTIVVTAGPAEPAPLLYLAPYAGAAMGEEFM

MNGKHVLIVYDDLSKQATAYRELSLILRRPPGREAYPGDVFYLHSRLLER

AAKLSDELGGGSMTALPIIETQAGDISAYIPTNVISITDGQIFLDSDSFY

SGVRPAIDAGASVSRVGGDAQIKAMKSVAGTLRLDLASYRELESFSQFGS

DLDAATQAKLNRGQRIVEVLKQPVHSPLKVEEQVMILYALTNGYLDKVAV

DDIARYQSELFEFIHASHQDLFDTILATKKLPEADKMNGALDAFAEQFQP

TAAAAK

SEQ ID NO: 6: forward primer
Primer-F: TCAACCAGTTGACGGTTCAG

SEQ ID NO: 7: reverse primer
Primer-R: TTTGGTTCAAAATGGCATCA
```

Deposit and Expert Solution

The following deposit was made according to the Budapest treaty on the international recognition of the deposit of microorganisms for the purposes of patent procedure.

*Lactobacillus plantarum* strain (DGCC12411) deposited under accession number DSM32493 on Apr. 26, 2017, at the DSMZ [Deutsche Sammlung von Mikroorganismen and Zellkulturen GmbH, Inhoffenstrasse 7B, D-38124 Braunschweig—Germany].

It is requested that the biological material shall be made available only by the issue of a sample to an expert nominated by the requester. In respect to those designations in which a European Patent is sought, a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

Various preferred features and embodiments of the present invention will now be described by way of non-limiting examples.

EXAMPLES

Example 1

Selection of a *Lactobacillus plantarum* with High Ropiness on MRS

The following method was used for screening *Lactobacillus plantarum* strains of the DuPont collection. Thus, 214 *Lactobacillus plantarum* isolated from various sources were screened as follows:

a single colony of each *L. plantarum* was inoculated into MRS agar plate, and incubated at 30° C. for 2 days;

the ropiness was manually scored based on the strength of filament formed when touch the colony by an inoculation loop, according to the following classification: no detectable ropiness (no filament formed), low ropiness, intermediate ropiness or high ropiness (see respectively FIG. 1A to 1D).

From the 214 tested strains, the following classification was obtained:
- 1 strain was classified with a high ropiness
- 2 strains were classified with intermediate ropiness
- 17 strains were classified with low ropiness
- 194 strains were classified with no detectable ropiness One *L. plantarum* strain representative of each class was then assayed for rheological and sensory analyses.

Example 2

Rheological Properties of Milk Fermented with DSM32493 and Comparison with 3 Other *L. plantarum* Strains 4 *L. plantarum* strains selected from example 1 were used to ferment milk and the rheological properties of the obtained fermented milks were determined.

Strains: The following strains were used:
- the DSM32493 strain, showing a high ropiness in example 1;
- the LP12111 strain showing an intermediate ropiness in example 1;
- the LP12428 strain showing a low ropiness in example 1;
- the *L. plantarum* 115 strain (also known as DGCC4715, deposited as DSM22266 in patent EP2245943B1) showing no detectable ropiness in example 1.

The following Test A was carried out:

Milk: 2 L UHT milk (3.2% protein, 3.5% fat) added with 6% sucrose and 0.1% of yeast extract powder (LP0021) from Oxoid™ was heat treated at 85° C. for 15 min and cooled down to room temperature.

Fermentation: For each strain, a frozen culture was inoculated into milk at $1.10^7$ CFU/mL. The inoculated milk was then fermented at 30° C. to reach pH 4.5 (typically about 22-24 h).

Rheological measurements: After fermentation, the samples were stirred by a rotator (RZR 2051 control, Heidolph) at 100 rpm for 1.5 min and stored at 4° C. for overnight, before measurement by rheometer. The used tank and bladder are as disclosed in FIG. 8. The samples were assessed by a rheometer (Anton Paar MCR 302, CC27-SN27450, Austria) using a coaxial cylinder C-CC27-T200/SS and a bob-cup. The rheometer was set to a constant temperature of 10° C. during the measurement. Settings were as follows:
- holding time (to rebuild to somewhat original structure): 10 minutes, without any physical stress applied to the sample.
- 25 measuring points over 500 s (one every 20 s)
- rotation step (to measure the shear stress at 11.6 1/s, the shear stress at 200 1/s and the difference of the shear stress at 146 1/s minus the shear stress at 41.1 1/s)
- Two steps were designed:
  - Shear rate: d(gamma)/dt=[0.1-200] 1/s log and [200-0.1] 1/s log
  - Each step contained 25 measuring points over 500 s (on every 20 s)

Figure 1:
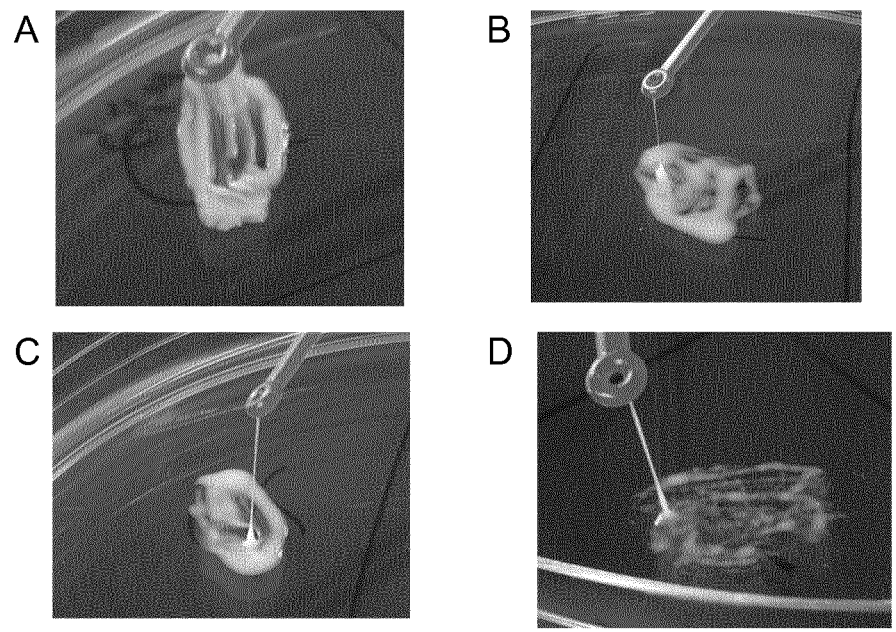
FIG. 1 represents photographs of ropiness assay on *L. plantarum* strains carried out on agar plate. (A) no detectable ropiness; (B) low ropiness; (C) intermediate ropiness; (D) high ropiness.
Figure 2:
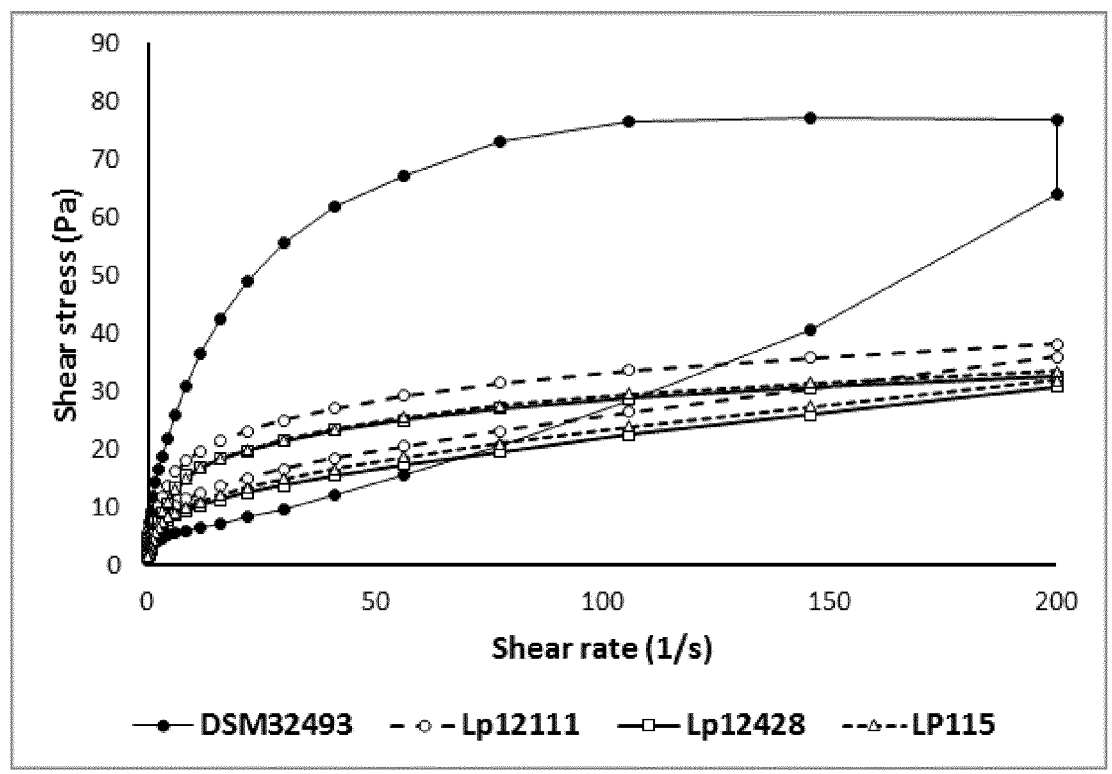
FIG. 2 shows flow curves of fermented milks obtained using 4 different *L. plantarum* strains.

The flow curves of fermented milks obtained using either the DSM32493 strain, the LP12111 strain, the LP12428 strain or the Lp115 strain were obtained (FIG. 2). As show in FIG. 2, as compared to the LP12111, LP12428 and Lp115 strains which share close flow curves, the flow curve of the DSM32493 strain is atypical due to its significantly higher thickness and ropiness.

For each fermented milk, the shear stress at 11.6 1/s, the shear stress at 200 1/s and the difference between the shear stress at 146 1/s and the shear stress at 41.1 1/s were then calculated (Table 1). The shear stress at 11.6 1/s was correlated to sensory thickness, the shear stress at 200 1/s was correlated to mouth-thickness and the difference between the shear stress at 146 1/s and the shear stress at 41.1 1/s was correlated to ropiness.

TABLE 1 shear stress at 11.6 1/s, shear stress at 200 1/s and difference between the shear stress at 146 1/s and the shear stress at 41.1 1/s of fermented milks obtained with either the DSM324931 strain, the LP12111 strain, the LP12428 strain or the Lp115 strain.

| Strain | Thickness (shear rate[1/s] 11.6) | Mouth thickness (shear rate[1/s] 200) | Ropiness (Δ146-41.1) |
|---|---|---|---|
| DSM32493 | 36.6 | 77 | 15.5 |
| LP12111 | 19.7 | 38.1 | 8.7 |
| LP12428 | 16.9 | 32.6 | 7.3 |
| Lp115 | 16.8 | 33.5 | 8 |

As detailed in Table 1, the fermented milk obtained using DSM32493 shows high values of thickness, mouth thickness and ropiness, almost double those obtained using LP12111, LP12428 and Lp115 strains.

Thus, these results show that a fermented milk having high values of thickness, mouth thickness and ropiness (as defined herein) can be obtained using a *L. plantarum* of the invention (in particular the DSM32493 strain).

Interestingly and as an advantage of the invention, these results also show that a fermented milk having high values of thickness, mouth thickness and ropiness (as defined herein) can be obtained using a pure culture of *L. plantarum* of the invention (in particular a pure culture of the DSM32493 strain). This is in contrast with fermented milk obtained with compositions described in the literature which comprise several strains (of which at least a *Streptococcus thermophilus* strain).

Example 3

Figure 3:
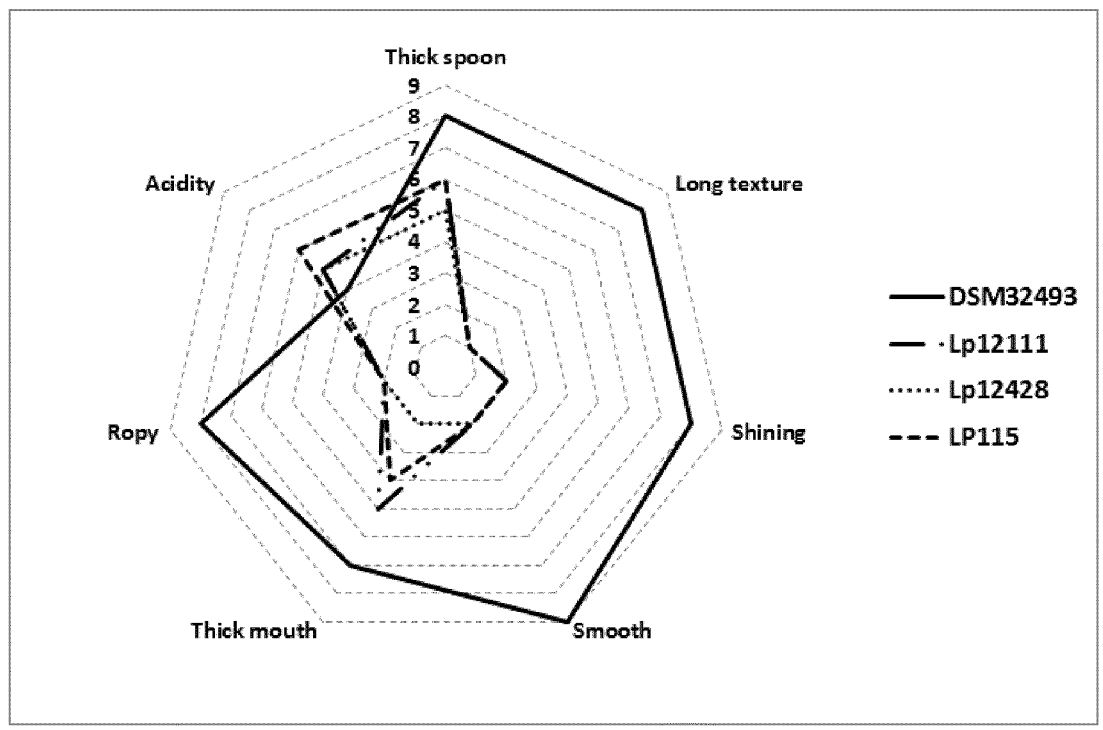
FIG. 3 is a schematic representation of the organoleptic properties of fermented milks obtained using 4 different *L. plantarum* strains.
Figure 4:
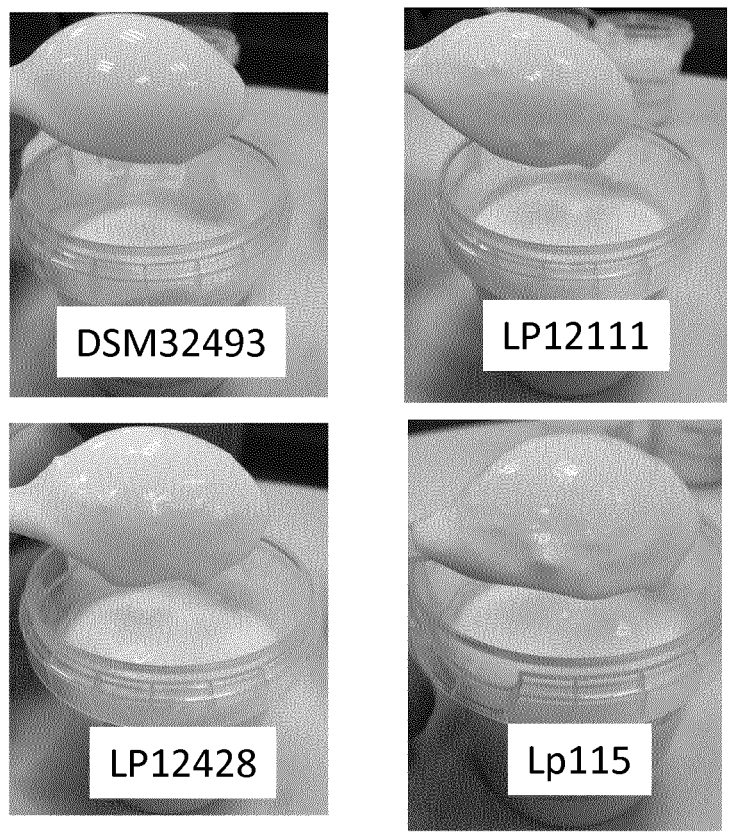
FIG. 4 represents photographs showing the appearance of fermented milks obtained using 4 different *L. plantarum* strains.

Sensory Analysis of Milk Fermented with DSM32493 and Comparison with 3 Other *L. plantarum* Strains An expert panel comprised of five culture/dairy application specialists evaluated the sensory properties of each fermented milk obtained using the DSM32493 strain, the LP12111 strain, the LP12428 strain or the Lp115 strain. Seven flavour and texture descriptors were evaluated and reported on a spider chart (FIG. 3). Whereas the fermented milks obtained using LP12111, LP12428 and Lp115 strains show comparable charts, the fermented milk obtained using the DSM32493 strain shows significant differences in several of these descriptors. Thus, fermented milks obtained using one of LP12111, LP12428 and Lp115 strains show grainy texture (so a non-shining appearance), low ropiness and smoothness, and low to medium thickness in mouth and spoon. In contrast, fermented milk obtained using the DSM32493 strain shows very high thickness in mouth and spoon, a very long texture, high ropiness and smoothness and has a shining appearance. Appearance of fermented milks obtained using either the DSM32493 strain, the LP12111 strain, the LP12428 strain or the Lp115 strain is shown in FIG. 4.

Example 4

Figure 5:
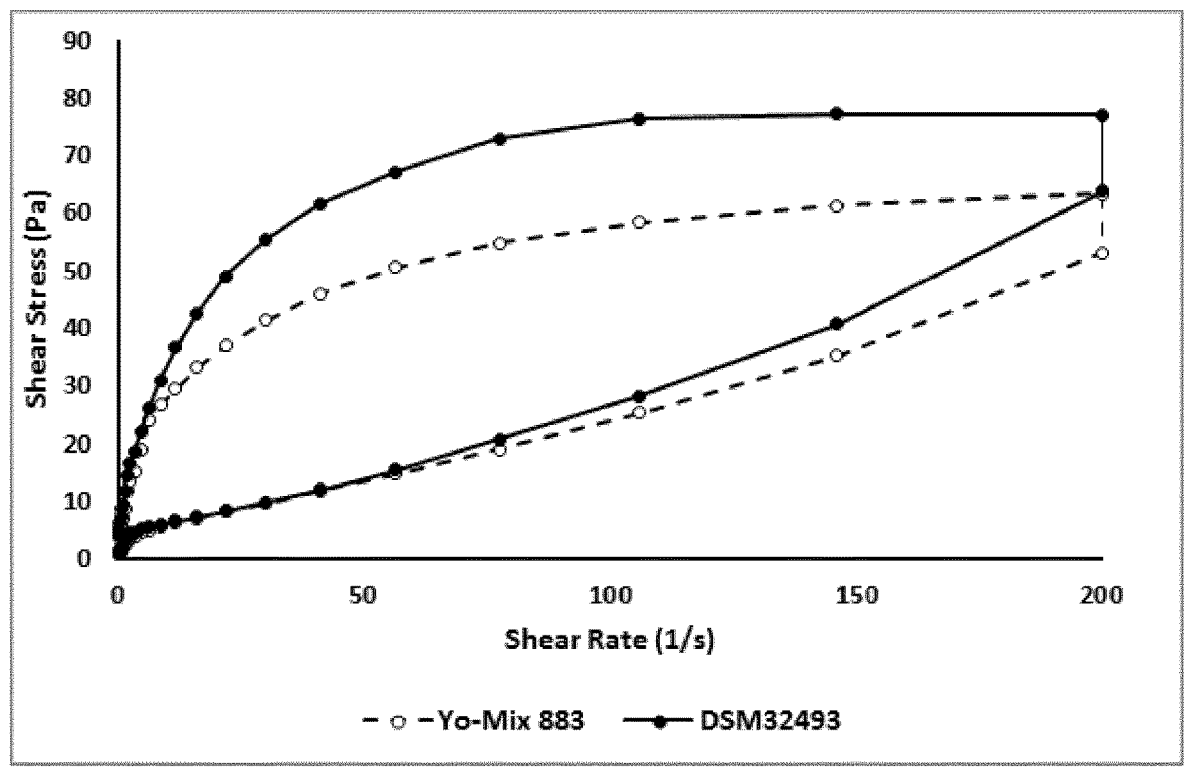
FIG. 5 shows the flow curve of a fermented milk obtained using a *L. plantarum* strain of the invention compared to a flow curve of a fermented milk obtained using a traditional starter culture.

Rheological Properties of Milk Fermented with DSM32493 Strain and Comparison with a Traditional Starter The rheological properties of a fermented milk obtained using DSM32493 was then compared with the ones of a milk fermented using a commercial yogurt starter culture with strong texturing property (Danisco; YO-MIX® 883) consisting of a combination of *Streptococcus thermophilus* and *Lactobacillus delbrueckii* subsp *bulgaricus* strains. Test A as described in example 2 was carried out, with inoculation of either the DSM32493 strain or the YO-MIX® 883 culture, and the flow curve of the fermented milks were obtained (FIG. 5). For each fermented milk, the shear stress at 11.6 1/s, the shear stress at 200 1/s and the difference between the shear stress at 146 1/s and the shear stress at 41.1 1/s were then calculated (Table 2).

TABLE 2 shear stress at 11.1 1/s, shear stress at 200 1/s and difference between the shear stress at 146 1/s and the shear stress at 41.1 1/s of fermented milks obtained with either the DSM324931 strain or the YO-MIX ® 883 culture.

| Culture | Thickness (shear rate[1/s] 11.6) | Mouth thickness (shear rate[1/s] 200) | Ropiness (Δ146-41.1) |
|---|---|---|---|
| DSM32493 | 36.6 | 77 | 15.5 |
| YO-MIX ® 883 | 29.5 | 63.4 | 15.5 |

As show in FIG. 5 and detailed in Table 2, the DSM32493 strain alone is sufficient to manufacture a fermented milk with a thickness and ropiness as good as the ones obtained using a traditional culture of *S. thermophilus* and *L. bulgaricus*. Moreover, this comparative example confirms the uniqueness of the DSM32493 strain to give a fermented milk with a high mouth-thickness.

Figure 6:
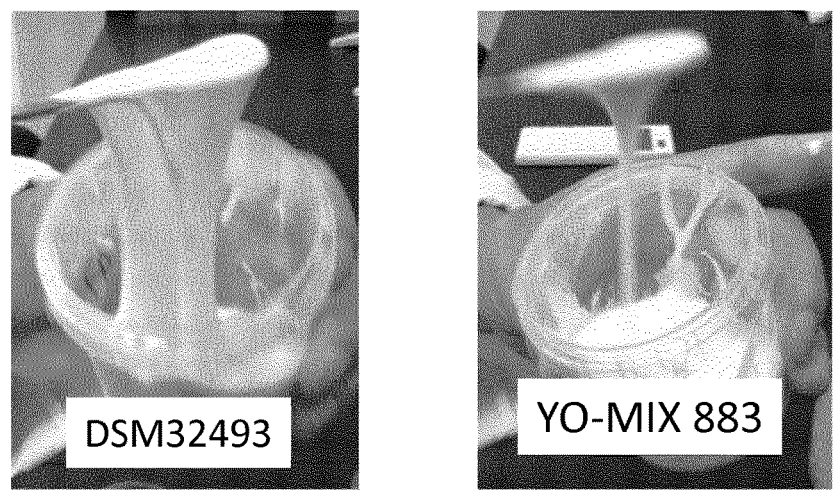
FIG. 6 represents photographs showing the long texture descriptor of a fermented milk obtained using a *L. plantarum* strain of the invention as compared to a fermented milk obtained using a traditional starter culture.

This high mouth-thickness value provided by the DSM32493 strain is confirmed by the long texture clearly visible on the left photograph of FIG. 6 as compared to the right photograph [obtained using YO-MIX® 883].

These results confirm that the DSM32493 is industrially interesting to obtain fermented milk presenting a high thickness, a high ropiness and a high mouth-thickness.

Example 5

Selection of a Low Post-Acidification *L. plantarum* Variant of the DSM32493 Strain The DSM32493 strain was streaked on MRS agar plate and anaerobically incubated at 30° C. for 2 days. A single colony was picked up and grew in 10 mL MRS broth 30° C. overnight. 200 µL of fresh culture (O.D=0.8) was inoculated into 10 mL of 0.5× MRS containing 700 µg/mL of neomycin, and then incubated at 30° C. for 2 days. A serial dilution of the fresh culture was prepared and plated on 0.5× MRS agar plate with 700 µg/mL of neomycin and incubated at 30° C. for 2 days. Single colonies were picked up, and each inoculated into both of 0.5× MRS (pH 6.3) and 0.5× MRS (pH adjusted to pH 4.5) in 96-well plates and incubated at 30° C. for 2 days. Colonies which grew in 0.5× MRS (pH 6.3) but not 0.5× MRS (pH 4.5) were selected. The acidification curve of each selected colony in MRS at 30° C. was monitored using iCinac for 4 days. Colonies with significant higher end pH (and considered as low post acidification mutants at fermentation temperature) were selected and their DNA sequenced.

One mutant (Lp12733) selected by the protocol described above was shown to contain the mutation G to A in position 506 of the ATP synthase alpha subunit gene of the ATP-synthase operon, resulting in the substitution of the glycine residue at position 169 by an aspartic acid residue. Presence of this mutation can be checked by PCR using the primers as defined in SEQ ID NOs: 6 and 7, and then DNA sequencing using the primer as defined in SEQ ID NO:6.

Figure 7:
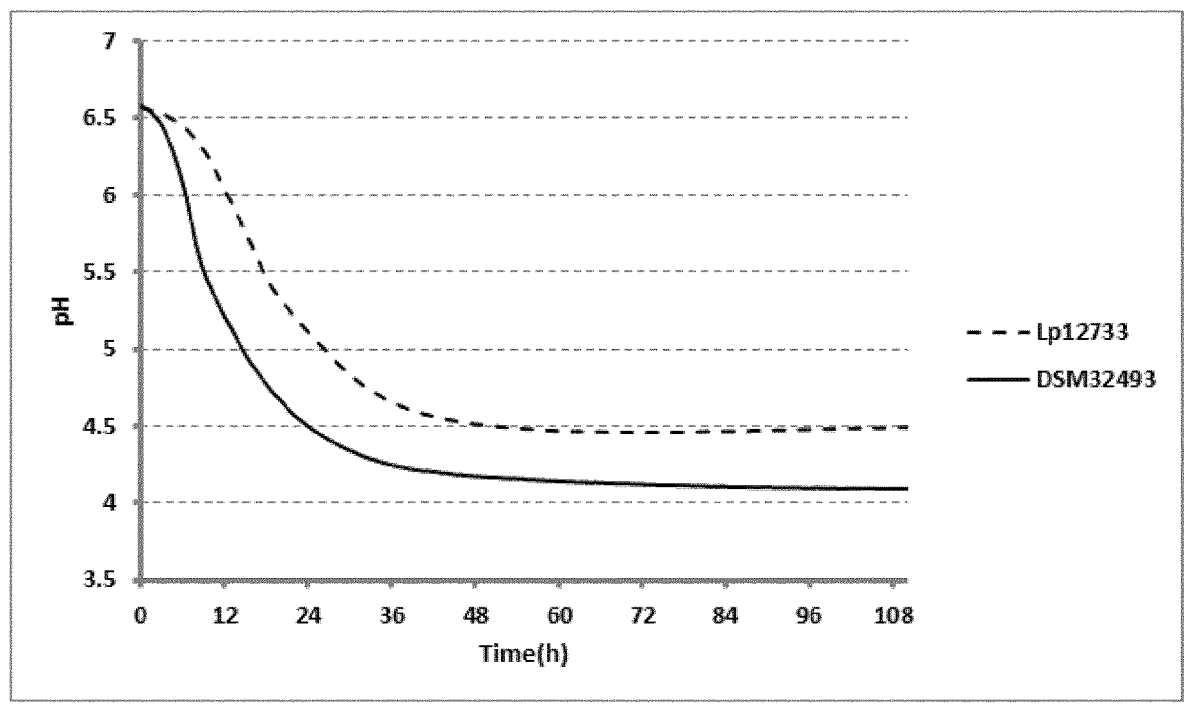
FIG. 7 shows the acidification profile (variation of pH over time) of milk fermented with two different *L. plantarum* strains of the invention.

The DSM32493 strain and its low post acidification mutant Lp12733 were used to ferment milk and the pH was recorded over time, using Test B described herein. Cinac curves were obtained and are shown in FIG. 7.

Test B:

Milk: UHT milk (3.2% protein, 3.5% fat) added with 6% sucrose and 0.1% of yeast extract powder (LP0021) from Oxoid™ was heat treated at 85° C. for 15 min and cooled down to room temperature.

Fermentation: For each strain, a freeze-dried culture was inoculated into milk at $1.10^7$ CFU/ mL and the inoculated milk placed at 37° C. (t=0). The inoculated milk was fermented until a pH of 4.5 ($t_{pH4.5}$) is reached and kept at 37° C. for at least 48 hours, and the pH of the milk continuously monitored.

Post-acidification measurements: The delta pH (ΔpH=pH at ($t_{pH4.5}$+48 h)−pH 4.5) was used to represent the post-acidification at fermentation temperature.

As shown in FIG. 7, the pH of fermented milk obtained using the DSM32493 strain at $t_{pH4.5}$+48 h hours is 4.1 whereas the pH of the fermented milk obtained using the Lp12733 strain (low post acidification mutant of the DSM32493 strain) is 4.5 (i.e. the pH of the fermented milk is steady at pH 4.5). Thus, the ΔpH of the DSM32493 strain is about 0.4, whereas the ΔpH of the Lp12733 strain is 0.

These results confirm that the Lp12733 strain (low post acidification mutant of the DSM32493) is industrially interesting to obtain fermented milk not only presenting a high thickness, a high ropiness and a high mouth-thickness, but also having a low post-acidification at fermentation temperature.

The invention claimed is:

1. A method for manufacturing a fermented dairy product, wherein:
the method comprises:
a) inoculating a milk substrate with a Lactobacillus plantarum strain which is the strain DSM32493 deposited at the DSMZ on Apr. 26, 2017, or a variant of the DSM32493 strain deposited at the DSMZ on Apr. 26, 2017 with a genome sequence identity of at least 95% to the genome sequence of the DSM32493 strain, wherein the variant is produced by spontaneous mutation or genetic engineering of the DSM32493 strain, and
b) fermenting the inoculated milk substrate to obtain a fermented dairy product; and
the Lactobacillus plantarum strain is characterized as, when inoculated into milk, generating a fermented milk that exhibits the following rheological features, as assayed by test A:
a) a shear stress measured at shear rate 11.6 s-1 higher than 30 Pa,
b) a shear stress measured at shear rate 200 s-1 higher than 60 Pa, and
c) a difference of the shear stress measured at 146 s 1 minus the shear stress measured at 41.1 s-1 higher than 12.

2. The method according to claim 1, wherein the Lactobacillus plantarum strain is further characterized by being a low post acidification strain at fermentation temperature.

3. The method according to claim 2, wherein the Lactobacillus plantarum strain is mutated within the ATP-synthase operon.

4. The method of claim 3, wherein the Lactobacillus plantarum strain bears a mutation in the ATP synthase alpha subunit gene of the ATP-synthase operon.

5. The method of claim 4, wherein the Lactobacillus plantarum strain bears a mutation G to A at its position 506.

6. The method according to claim 1, wherein the Lactobacillus plantarum strain is inoculated into the milk substrate in combination with at least one other lactic acid bacteria.

7. The method of claim 6, wherein the other lactic acid bacteria is a Lactobacillus delbrueckii subsp bulgaricus strain.

8. The method according to claim 1, wherein the Lactobacillus plantarum strain is inoculated together with a booster.

9. The method according to claim 8, wherein the booster comprises a yeast extract or an amino-acid-containing composition.

10. The method according to claim 1, wherein the variant has a genome sequence identity of at least 99% to the genome sequence of the DSM32493 strain.

* * * * *

SEQUENCE LISTING

<160> NUMBER OF SEQ ID NOS: 7

<210> SEQ ID NO 1
<211> LENGTH: 6453
<212> TYPE: DNA
<213> ORGANISM: Lactobacillus plantarum

<400> SEQUENCE: 1

| | | | | | |
|---|---|---|---|---|---|
| gtgggtgatc | cagttcctac | agtcaaattc | cttggactga | cgtttaatat | cgcgaatgac | 60 |
| atctcagtaa | ttgtgacttg | tctgattgtt | ttcttgtttg | ttttttttact | ttcgcgacat | 120 |
| ttaacaatga | agcccaaggg | tggacaaaat | gtgctggagt | ggctcatcga | gttcacgaat | 180 |
| ggcattgtca | aagggtcgat | caagggtaac | gaagcgtcta | acttcggttt | gtacgcattt | 240 |
| acattgtttc | tctttatctt | catcgctaac | caacttggat | tgttcattca | cgttcaggtc | 300 |
| gggcagtata | cgtatctgaa | gagtccaacc | gccgatccga | ttgtgacttt | gacgttatcg | 360 |
| tttatgaccg | ttgcacttgc | acatgctgcg | ggtgttcgta | agaaaggtat | gggtggttat | 420 |
| ttgaaagaat | acacacaacc | ttttgctgtt | ttctcggttg | ttaacgtctt | tgaacaattt | 480 |
| accgatttcc | taactttagg | tcttcggctg | ttcgggaaca | tctttgctgg | tgaaatgtta | 540 |
| ctaacgaagg | ttgctgattt | ggcaaagagc | aacggttggt | tgagctatgt | ttactcattt | 600 |
| ccaattgaac | tcttatggca | aggtttctca | gtgtttatcg | ggagcattca | agcgttcgtg | 660 |
| ttcgtaacct | tgacttcagt | ttatatttct | cagaaggtta | acgacgagga | ataatttcta | 720 |
| gttttttaat | tttaaggagg | atacacagat | tatgggagca | attgctgcag | gtattgctat | 780 |
| gtgtggtgcc | gctataggtg | ctggtattgg | taacggtttg | gttatttcta | agatgcttga | 840 |
| agggatggcc | cgtcaaccag | aattatctgg | tcaattacgg | actaacatgt | tcatcggtgt | 900 |
| tgggttggtc | gaatcaatgc | ctataatttc | cttcgttgtt | gctttgatgg | ttatgaacaa | 960 |
| gtaatcattg | gtcaacgagt | tcattttaat | gaaaatgaaa | gaaggaggtg | tcattagatg | 1020 |
| ctctcgcatt | taattatcgg | tgcatccggt | ctctaccttg | gtgatatgtt | gtttatcggg | 1080 |
| attagcttta | ttgttttgat | ggcattgatc | tctgttgttg | cttggaagcc | catcacaaaa | 1140 |
| atgatggctg | atcgagccga | caagattgcg | aacgacattg | attcagcaca | aaagtctcgg | 1200 |
| caagaagcga | gtgacttagc | tgatcaacgg | cgtgatgcgc | tatcacactc | tcgcgctgaa | 1260 |
| gcgagtgaaa | ttgtcgctga | cgcgaaaaag | agtggcgaaa | agcaacggtc | aagtatcatt | 1320 |
| gccgatgcgc | aaaacgaagc | aacgcagtat | aaacaaaatg | cgcgtaagga | tattgaacag | 1380 |
| gagcgtcaag | atgccttgaa | gaacgtccaa | tcagacgtcg | ctgacatttc | gattgcgatt | 1440 |
| gctacgaaga | ttattaagaa | gcaattggat | ccggaaggcc | aacaggcatt | aattaattcg | 1500 |
| tatattgaag | ggttgggaaa | gcatgagtct | tgataatctt | acaattgcaa | gtcgttattc | 1560 |
| aaaggcactc | tttgaacttg | cagttgaaaa | agatcagacc | gaagcattcc | tggccgagtt | 1620 |
| aaagcaatta | cggcaagtct | tgtcgacaa | cccgcaattg | gcagaggtcc | tctcaggatc | 1680 |
| attgcttccg | gttgatcaaa | aacagacaac | gttgtcaact | ttgactgacc | acgcttcaga | 1740 |
| atacattaaa | aactttattc | aaatgttgta | tgattacggc | cgcatgtcga | acttagttgg | 1800 |
| cattgttgac | gcgtttgaag | cacgtttcga | tgagagtcgc | aaaatagtgc | atgccgaagt | 1860 |
| aacgtctgcg | gtcaagttgt | cagatgagca | agctgatgca | atcgcaaagg | cattcgccaa | 1920 |
| acgtgttggg | gccaatcagg | ttgttttgtc | acgtaaagtc | gatgaagcaa | tcattggcgg | 1980 |
| tgtaattgtg | aagtcaaaata | atcaaacgtt | tgatggtagc | gttgcgttac | aactaacgaa | 2040 |
| tttaagacga | gcactcatca | acaattagtt | tacgaagagg | tgaaactttt | atgagcatta | 2100 |

```
aatctgaaga aatcagtgct ctaatcaaac aacaattaga aagttatcaa actgagctct    2160
cagttgctga aaccggtact gtcacctacg ttggtgatgg gatcgcccgt gctcacggac    2220
tcgacaacgc cttacaaggt gaattactcg aattcagtaa cggagtttac gggatggtac    2280
aaaacctcga aagcaacgat gttggtatcg ttgttttagg ggattttgat ggtattcgtg    2340
aaggcgatac tgttaagcgg actggccgca tcatggaagt tccagtcggt gacgccatga    2400
ttggccgggt cgttaaccca ttaggtcaac cagttgacgg ttcaggtgag attaagacca    2460
cgaatacgcg gccaatcgaa cataaagctc ctggtattat gcaacggcaa tcagttagcg    2520
aaccacttca aactgggatc aaggccattg atgccttagt tccaattggt cggggccaac    2580
gtgaattgat tatcggtgac cgtaagactg ggaagacgtc cgttgccatt gatgccattt    2640
tgaaccaaaa ggaccaagac atgatttgtg tctacgttgc aatcggtcaa aaggactcaa    2700
ctgtacgggc ccaagttgaa acgttgaaga agttaggtgc gatggactac acaatcgttg    2760
taactgccgg acctgctgaa ccagcgccat tactgtactt agctccttat gctggggcag    2820
cgatgggtga agaatttatg atgaacggca agcacgtttt gatcgtctat gatgaccttt    2880
caaagcaagc aacggcttac cgtgaacttt ccttgatcct ccgtcgtcct ccaggtcgtg    2940
aagcttatcc tggggatgtc ttctacttgc actcacggtt actcgaacgg gctgccaagt    3000
tgagcgatga attgggtggc ggttcaatga cggccttacc aattatcgaa acgcaagctg    3060
gggatatttc ggcttatatt ccaactaacg ttatttcaat caccgatggg caaatcttct    3120
tggatagtga ttcattctat tcaggtgtgc ggccagcgat tgatgccggg gcctctgttt    3180
cccgggttgg tggggatgcg caaattaaag cgatgaagtc cgttgccggg accttgcgtc    3240
ttgacttggc ttcttatcgt gaattggaat ccttctcaca attcggttct gacttggatg    3300
ctgcaaccca agcgaaatta atcgtgggc aacggatcgt tgaagtctta aaacaacctg    3360
ttcattcacc attgaaggtc gaagaacaag taatgatttt atatgctttg accaacggtt    3420
atttggataa agtggcagtt gatgatattg cccgttacca aagtgaattg tttgaatta    3480
ttcatgctag tcatcaggac ctctttgata cgattttggc aaccaagaag ttaccagaag    3540
ctgataagat gaatggggcc ttagatgcgt ttgcagaaca attccagcca accgctgccg    3600
ctgcgaagta gttatggctg aaaaggatgg tgagtagtgc atggcagaat cattaatgga    3660
tgtcaagcgc cgaattgact caacaaagaa gactcatcaa attacgtcgg caatgcaaat    3720
ggtctcaact tcaaaattga accagattca aaagcatacc agcacgtatc aggtgtacgc    3780
ttctaaagtt gaaagcatcg tttcacatct tgccaaagct catctgatgt cagcaagtgc    3840
cggtgttgct aacagtaatt cgaacacgat ttcagttagt gaattgctcg cgcaacgccc    3900
cgttaaaaag actggtttat tggtgatcac ttcggaccgt ggcctcgttg gtagttacaa    3960
cagtaacgtg ttgaaacaga ctaacgattt catgcggacg cacaaggttg atgccgataa    4020
cgcagtcgtt ttggcggttg gtggcactgg tgcggatttc tataaaaaga acgggttaaa    4080
cgtggcttat gagtaccgcg gcgtctctga tgtcccaact tttaaagagg ttcgtgaaat    4140
cgttaagaca gtcacatcaa tgtaccacaa cgaagtcttt gatgaacttt acgtcttcta    4200
caaccacttt attaatcggc tctcttctgg ttttcgggcc gttaagatgt taccgatctc    4260
cgaagagacc tttgaacaaa gtgagtcaga taatcgtaaa gccaaggata gccgggtaga    4320
tgtcggtccc gagtatgaaa tggaaccgtc agaagaagcc attttgtcgg ccgtgttgcc    4380
acaatatgct gaaagcttgg tttatggtgc aatcttggat gccaagactg ctgaacatgc    4440
```

```
ttcgtcgtca accgcgatga aggctgcatc agataacgct ggcgatttaa tcgataaatt    4500
aaatctgaaa tataaccgtg cgcgtcaagc tgctattacc actgaaatca ctgaaatcac    4560
tggtggtttg gttgcgcaag aataacgaag tgggaggaat aacgactaa tgagtacagg     4620 taaagttgta caagttattg gacccgttgt tgacgttgaa ttctctctaa acgataagtt    4680
acccgatatt aataacgcct tgatcattca gaaggacaac gatgacactt taacggtgga    4740
agtatcgttg gaattaggtg atggggttgt tcggaccgtc gcgatggatg gtacggatgg    4800
cttgcgccgg ggaatgacag ttgaagacac tggttcttca attactgttc ccgttggtaa    4860
agagacgtta ggccgggtct tcaacgtttt aggggaaacc attgatggtg gtccagaatt    4920
cggtccagac gcagaacgta acccgattca tcgggatgcg cctaaatatg atgaattaac    4980
gaccagtact gaagtattgg aaactggaat taaagttatt gacctcttag caccttatgt    5040
tcgtggtggt aagattgggt tgttcggtgg tgccggtgtt ggtaaaactg ttttaatcca    5100
ggaattaatt cataacattg cccaagaaca taacgggatt tccgtgttta ccggtgttgg    5160
tgaacggacg cgtgaaggga atgacccttta cttcgaaatg aaggcttccg gcgttttgaa   5220
gaataccgcc atggtttatg gtcaaatgaa cgaaccacct ggtgcccgga tgcgggtggc    5280
cttgaccggt ttgacgattg cggaatactt ccgtgatgtt caaggtcaag acgtgttgtt    5340
attcatcgac aatatcttcc ggttcacgca agctggttct gaagtttccg ccttacttgg    5400
tcggattcct tcagccgttg gttaccaacc aaccttagcc actgaaatgg gtcaattaca    5460
agaacggatc acttctacca agaagggggtc agttacttcg attcaagccg tttatgtacc    5520
tgccgatgat tataccgacc cggcacctgc aacgactttc gcccatttgg atgcgacgac    5580
caacttggaa cgttctttga cggaacaagg gatctaccca gccgttgacc cattagcttc    5640
ttcttcaatc gctctggacc catcaatcgt gggcgaagaa cattatcaag ttgcaacgga    5700
agttcaacgg gtcttgcaac gttatcgtga attgcaagat attatctcga ttttagggat    5760
ggatgaatta tctgacgaag aaaagacaac tgttgcgcgt gcacggcgga ttcaattctt    5820
cttgtcacaa aacttcttcg ttgccgaaaa ctttacgggc caacctggtt cgtatgtgcc    5880
aatcaacgat accatcaagg gcttcaaaga aattcttgaa ggtaaatatg atgacctacc    5940
agaagacgca ttccgtcaag ttggtaagat cgacgacgtg gtcgaaaaag cgaaatcgat    6000
ggtaactgat taggaggggt ttacatggct gacaatgcaa aatcattaac cgttagcatc    6060
gtaactccag acggtcaggt ctatgagaat aagacgccaa tgttgatcgt gcgaacgatt    6120
gacggcgaac tcgaatttt gccgaaccat attcctgtga ttgcatcgct tgcaatcgat    6180
gaggttcgga tcaagcaact tgaaagtgat caggaagatg acgaaattgc cgttaatggt    6240
ggttttgttg agttcagtaa taatacggca acgattgttg ccgatagtgc tgaacgtcag    6300
aatgacattg acgttgctcg agctgaaaat gcacggaaac gcgctgaaac acggattcaa    6360
aatgcccaac aaaagcacga tgatgctgag ttggcgcggg cccaagtcgc tttgcggcgt    6420
gccatgaacc gtttgaatgt tgctcggcat taa                                 6453

<210> SEQ ID NO 2
<211> LENGTH: 1521
<212> TYPE: DNA
<213> ORGANISM: Lactobacillus plantarum

<400> SEQUENCE: 2
atgagcatta aatctgaaga aatcagtgct ctaatcaaac aacaattaga aagttatcaa      60
actgagctct cagttgctga aaccggtact gtcacctacg ttggtgatgg gatcgcccgt     120
```

```
gctcacggac tcgacaacgc cttacaaggt gaattactcg aattcagtaa cggagtttac    180
gggatggtac aaaacctcga aagcaacgat gttggtatcg ttgttttagg ggattttgat    240
ggtattcgtg aaggcgatac tgttaagcgg actggccgca tcatggaagt tccagtcggt    300
gacgccatga ttggccgggt cgttaaccca ttaggtcaac cagttgacgg ttcaggtgag    360
attaagacca cgaatacgcg gccaatcgaa cataaagctc ctggtattat gcaacggcaa    420
tcagttagcg aaccacttca aactgggatc aaggccattg atgccttagt tccaattggt    480
cggggccaac gtgaattgat tatcggtgac cgtaagactg gaagacgtc cgttgccatt     540 gatgccattt tgaaccaaaa ggaccaagac atgatttgtg tctacgttgc aatcggtcaa    600
aaggactcaa ctgtacgggc ccaagttgaa acgttgaaga gttaggtgc gatggactac     660 acaatcgttg taactgccgg acctgctgaa ccagcgccat tactgtactt agctccttat    720
gctggggcag cgatgggtga agaatttatg atgaacggca agcacgtttt gatcgtctat    780
gatgaccttt caaagcaagc aacggcttac cgtgaacttt ccttgatcct ccgtcgtcct    840
ccaggtcgtg aagcttatcc tggggatgtc ttctacttgc actcacggtt actcgaacgg    900
gctgccaagt tgagcgatga attgggtggc ggttcaatga cggccttacc aattatcgaa    960
acgcaagctg gggatatttc ggcttatatt ccaactaacg ttatttcaat caccgatggg   1020
caaatcttct tggatagtga ttcattctat tcaggtgtgc ggccagcgat tgatgccggg   1080
gcctctgttt cccgggttgg tggggatgcg caaattaaag cgatgaagtc cgttgccggg   1140
accttgcgtc ttgacttggc ttcttatcgt gaattggaat ccttctcaca attcggttct   1200
gacttggatg ctgcaaccca agcgaaatta aatcgtgggc aacggatcgt tgaagtctta   1260
aaacaacctg ttcattcacc attgaaggtc gaagaacaag taatgatttt atatgctttg   1320
accaacggtt atttggataa agtggcagtt gatgatattg cccgttacca aagtgaattg   1380
tttgaattta ttcatgctag tcatcaggac ctctttgata cgattttggc aaccaagaag   1440
ttaccagaag ctgataagat gaatggggcc ttagatgcgt tgcagaaca attccagcca    1500 accgctgccg ctgcgaagta g                                             1521
```

<210> SEQ ID NO 3
<211> LENGTH: 506
<212> TYPE: PRT
<213> ORGANISM: Lactobacillus plantarum

<400> SEQUENCE: 3

```
Met Ser Ile Lys Ser Glu Glu Ile Ser Ala Leu Ile Lys Gln Gln Leu
1               5                   10                  15

Glu Ser Tyr Gln Thr Glu Leu Ser Val Ala Glu Thr Gly Thr Val Thr
            20                  25                  30

Tyr Val Gly Asp Gly Ile Ala Arg Ala His Gly Leu Asp Asn Ala Leu
        35                  40                  45

Gln Gly Glu Leu Leu Glu Phe Ser Asn Gly Val Tyr Gly Met Val Gln
    50                  55                  60

Asn Leu Glu Ser Asn Asp Val Gly Ile Val Leu Gly Asp Phe Asp
65                  70                  75                  80

Gly Ile Arg Glu Gly Asp Thr Val Lys Arg Thr Gly Arg Ile Met Glu
                85                  90                  95

Val Pro Val Gly Asp Ala Met Ile Gly Arg Val Asn Pro Leu Gly
            100                 105                 110

Gln Pro Val Asp Gly Ser Gly Glu Ile Lys Thr Thr Asn Thr Arg Pro
```

```
            115                 120                 125
Ile Glu His Lys Ala Gly Ile Met Gln Arg Gln Ser Val Ser Glu
        130                 135                 140
Pro Leu Gln Thr Gly Ile Lys Ala Ile Asp Ala Leu Val Pro Ile Gly
145                 150                 155                 160
Arg Gly Gln Arg Glu Leu Ile Ile Gly Asp Arg Lys Thr Gly Lys Thr
                165                 170                 175
Ser Val Ala Ile Asp Ala Ile Leu Asn Gln Lys Asp Gln Asp Met Ile
                180                 185                 190
Cys Val Tyr Val Ala Ile Gly Gln Lys Asp Ser Thr Val Arg Ala Gln
            195                 200                 205
Val Glu Thr Leu Lys Lys Leu Gly Ala Met Asp Tyr Thr Ile Val Val
        210                 215                 220
Thr Ala Gly Pro Ala Glu Pro Ala Pro Leu Leu Tyr Leu Ala Pro Tyr
225                 230                 235                 240
Ala Gly Ala Ala Met Gly Glu Glu Phe Met Met Asn Gly Lys His Val
                245                 250                 255
Leu Ile Val Tyr Asp Asp Leu Ser Lys Gln Ala Thr Ala Tyr Arg Glu
                260                 265                 270
Leu Ser Leu Ile Leu Arg Arg Pro Gly Arg Glu Ala Tyr Pro Gly
            275                 280                 285
Asp Val Phe Tyr Leu His Ser Arg Leu Leu Glu Arg Ala Ala Lys Leu
        290                 295                 300
Ser Asp Glu Leu Gly Gly Gly Ser Met Thr Ala Leu Pro Ile Ile Glu
305                 310                 315                 320
Thr Gln Ala Gly Asp Ile Ser Ala Tyr Ile Pro Thr Asn Val Ile Ser
                325                 330                 335
Ile Thr Asp Gly Gln Ile Phe Leu Asp Ser Asp Ser Phe Tyr Ser Gly
                340                 345                 350
Val Arg Pro Ala Ile Asp Ala Gly Ala Ser Val Ser Arg Val Gly Gly
            355                 360                 365
Asp Ala Gln Ile Lys Ala Met Lys Ser Val Ala Gly Thr Leu Arg Leu
        370                 375                 380
Asp Leu Ala Ser Tyr Arg Glu Leu Glu Ser Phe Ser Gln Phe Gly Ser
385                 390                 395                 400
Asp Leu Asp Ala Ala Thr Gln Ala Lys Leu Asn Arg Gly Gln Arg Ile
                405                 410                 415
Val Glu Val Leu Lys Gln Pro Val His Ser Pro Leu Lys Val Glu Glu
                420                 425                 430
Gln Val Met Ile Leu Tyr Ala Leu Thr Asn Gly Tyr Leu Asp Lys Val
            435                 440                 445
Ala Val Asp Asp Ile Ala Arg Tyr Gln Ser Glu Leu Phe Glu Phe Ile
        450                 455                 460
His Ala Ser His Gln Asp Leu Phe Asp Thr Ile Leu Ala Thr Lys Lys
465                 470                 475                 480
Leu Pro Glu Ala Asp Lys Met Asn Gly Ala Leu Asp Ala Phe Ala Glu
                485                 490                 495
Gln Phe Gln Pro Thr Ala Ala Ala Lys
                500                 505

<210> SEQ ID NO 4
<211> LENGTH: 1521
<212> TYPE: DNA
<213> ORGANISM: Lactobacillus plantarum
```

<400> SEQUENCE: 4

```
atgagcatta aatctgaaga aatcagtgct ctaatcaaac aacaattaga aagttatcaa        60
actgagctct cagttgctga aaccggtact gtcacctacg ttggtgatgg gatcgcccgt       120
gctcacggac tcgacaacgc cttacaaggt gaattactcg aattcagtaa cggagtttac       180
gggatggtac aaaacctcga aagcaacgat gttggtatcg ttgttttagg ggattttgat       240
ggtattcgtg aaggcgatac tgttaagcgg actggccgca tcatggaagt tccagtcggt       300
gacgccatga ttggccgggt cgttaaccca ttaggtcaac cagttgacgg ttcaggtgag       360
attaagacca cgaatacgcg gccaatcgaa cataaagctc ctggtattat caacggcaa        420
tcagttagcg aaccacttca aactgggatc aaggccattg atgccttagt tccaattggt       480
cggggccaac gtgaattgat tatcgatgac cgtaagactg gaagacgtc cgttgccatt        540
gatgccattt tgaaccaaaa ggaccaagac atgatttgtg tctacgttgc aatcggtcaa       600
aaggactcaa ctgtacgggc ccaagttgaa acgttgaaga agttaggtgc gatggactac       660
acaatcgttg taactgccgg acctgctgaa ccagcgccat tactgtactt agctccttat       720
gctggggcag cgatgggtga agaatttatg atgaacggca agcacgtttt gatcgtctat       780
gatgaccttt caaagcaagc aacggcttac cgtgaacttt ccttgatcct ccgtcgtcct       840
ccaggtcgtg aagcttatcc tggggatgtc ttctacttgc actcacggtt actcgaacgg       900
gctgccaagt tgagcgatga attgggtggc ggttcaatga cggccttacc aattatcgaa       960
acgcaagctg gggatatttc ggcttatatt ccaactaacg ttatttcaat caccgatggg      1020
caaatcttct tggatagtga ttcattctat tcaggtgtgc ggccagcgat tgatgccggg      1080
gcctctgttt cccgggttgg tggggatgcg caaattaaag cgatgaagtc cgttgccggg      1140
accttgcgtc ttgacttggc ttcttatcgt gaattggaat ccttctcaca attcggttct      1200
gacttggatg ctgcaaccca agcgaaatta aatcgtgggc aacggatcgt tgaagtctta      1260
aaacaacctg ttcattcacc attgaaggtc gaagaacaag taatgatttt atatgctttg      1320
accaacggtt atttggataa agtggcagtt gatgatattg cccgttacca agtgaattg       1380
tttgaattta ttcatgctag tcatcaggac ctctttgata cgattttggc aaccaagaag      1440
ttaccagaag ctgataagat gaatgggggcc ttagatgcgt tgcagaaca attccagcca      1500
accgctgccg ctgcgaagta g                                                1521
```

<210> SEQ ID NO 5
<211> LENGTH: 506
<212> TYPE: PRT
<213> ORGANISM: Lactobacillus plantarum

<400> SEQUENCE: 5

```
Met Ser Ile Lys Ser Glu Glu Ile Ser Ala Leu Ile Lys Gln Gln Leu
1               5                   10                  15

Glu Ser Tyr Gln Thr Glu Leu Ser Val Ala Glu Thr Gly Thr Val Thr
            20                  25                  30

Tyr Val Gly Asp Gly Ile Ala Arg Ala His Gly Leu Asp Asn Ala Leu
        35                  40                  45

Gln Gly Glu Leu Leu Glu Phe Ser Asn Gly Val Tyr Gly Met Val Gln
    50                  55                  60

Asn Leu Glu Ser Asn Asp Val Gly Ile Val Val Leu Gly Asp Phe Asp
65                  70                  75                  80

Gly Ile Arg Glu Gly Asp Thr Val Lys Arg Thr Gly Arg Ile Met Glu
```

```
                 85                  90                  95
Val Pro Val Gly Asp Ala Met Ile Gly Arg Val Val Asn Pro Leu Gly
            100                 105                 110

Gln Pro Val Asp Gly Ser Gly Glu Ile Lys Thr Thr Asn Thr Arg Pro
            115                 120                 125

Ile Glu His Lys Ala Pro Gly Ile Met Gln Arg Gln Ser Val Ser Glu
            130                 135                 140

Pro Leu Gln Thr Gly Ile Lys Ala Ile Asp Ala Leu Val Pro Ile Gly
145                 150                 155                 160

Arg Gly Gln Arg Glu Leu Ile Ile Asp Asp Arg Lys Thr Gly Lys Thr
                165                 170                 175

Ser Val Ala Ile Asp Ala Ile Leu Asn Gln Lys Asp Gln Asp Met Ile
            180                 185                 190

Cys Val Tyr Val Ala Ile Gly Gln Lys Asp Ser Thr Val Arg Ala Gln
            195                 200                 205

Val Glu Thr Leu Lys Lys Leu Gly Ala Met Asp Tyr Thr Ile Val Val
            210                 215                 220

Thr Ala Gly Pro Ala Glu Pro Ala Pro Leu Leu Tyr Leu Ala Pro Tyr
225                 230                 235                 240

Ala Gly Ala Ala Met Gly Glu Glu Phe Met Met Asn Gly Lys His Val
                245                 250                 255

Leu Ile Val Tyr Asp Asp Leu Ser Lys Gln Ala Thr Ala Tyr Arg Glu
            260                 265                 270

Leu Ser Leu Ile Leu Arg Arg Pro Pro Gly Arg Glu Ala Tyr Pro Gly
            275                 280                 285

Asp Val Phe Tyr Leu His Ser Arg Leu Leu Glu Arg Ala Ala Lys Leu
            290                 295                 300

Ser Asp Glu Leu Gly Gly Gly Ser Met Thr Ala Leu Pro Ile Ile Glu
305                 310                 315                 320

Thr Gln Ala Gly Asp Ile Ser Ala Tyr Ile Pro Thr Asn Val Ile Ser
                325                 330                 335

Ile Thr Asp Gly Gln Ile Phe Leu Asp Ser Asp Ser Phe Tyr Ser Gly
            340                 345                 350

Val Arg Pro Ala Ile Asp Ala Gly Ala Ser Val Ser Arg Val Gly Gly
            355                 360                 365

Asp Ala Gln Ile Lys Ala Met Lys Ser Val Ala Gly Thr Leu Arg Leu
370                 375                 380

Asp Leu Ala Ser Tyr Arg Glu Leu Glu Ser Phe Ser Gln Phe Gly Ser
385                 390                 395                 400

Asp Leu Asp Ala Ala Thr Gln Ala Lys Leu Asn Arg Gly Gln Arg Ile
                405                 410                 415

Val Glu Val Leu Lys Gln Pro Val His Ser Pro Leu Lys Val Glu Glu
            420                 425                 430

Gln Val Met Ile Leu Tyr Ala Leu Thr Asn Gly Tyr Leu Asp Lys Val
            435                 440                 445

Ala Val Asp Asp Ile Ala Arg Tyr Gln Ser Glu Leu Phe Glu Phe Ile
450                 455                 460

His Ala Ser His Gln Asp Leu Phe Asp Thr Ile Leu Ala Thr Lys Lys
465                 470                 475                 480

Leu Pro Glu Ala Asp Lys Met Asn Gly Ala Leu Asp Ala Phe Ala Glu
                485                 490                 495

Gln Phe Gln Pro Thr Ala Ala Ala Lys
            500                 505
```

```
<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
tcaaccagtt gacggttcag                                          20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
tttggttcaa aatggcatca                                          20
```